US006211196B1

(12) United States Patent
Heitsch et al.

(10) Patent No.: US 6,211,196 B1
(45) Date of Patent: *Apr. 3, 2001

(54) BENZYLOXY-SUBSTITUTED, FUSED N-HETEROCYCLES, PROCESSES FOR THEIR PREPARATION, AND THEIR USE AS BRADYKININ RECEPTOR ANTAGONISTS

(75) Inventors: Holger Heitsch, Mainz-Kastel; Adalbert Wagner, Gersthofen; Klaus Wirth, Kriftel; Bernward Schölkens, Kelkheim, all of (DE)

(73) Assignee: Aventis Pharma Deutschland GmbH, Frankfurt am Main (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/048,305

(22) Filed: Mar. 26, 1998

(30) Foreign Application Priority Data

Mar. 27, 1997 (DE) ............................................. 197 12 960

(51) Int. Cl.[7] ..................... C07D 401/00; C07D 217/00; C07D 215/00; A61K 31/47; A61K 31/505; A61K 31/495; A61P 1/16; C07P 237/00

(52) U.S. Cl. ......................... 514/311; 546/174; 546/175; 546/177; 546/178; 546/146; 546/148; 546/149; 546/153; 546/155; 546/156; 546/157; 546/158; 546/159; 546/165; 546/166; 546/170; 546/172; 514/248; 514/249; 514/252.04; 514/255.05; 514/256; 514/259; 514/307; 514/312; 514/313; 514/314; 544/235; 544/237; 544/238; 544/283; 544/284; 544/333; 544/335; 544/336; 544/353; 544/363; 544/405

(58) Field of Search ..................... 544/235, 237, 544/238, 283, 284, 333, 335, 336, 353, 363, 405; 546/146, 148, 149, 153, 155, 156, 157, 158, 159, 165, 166, 170, 172, 174, 175, 177, 178; 514/248, 249, 256, 259, 307, 311, 312, 313, 314, 252.04, 255.05

(56) References Cited

U.S. PATENT DOCUMENTS

| 5,202,336 | * | 4/1993 | Mohrs et al. | .......................... 514/311 |
| 5,563,162 | * | 10/1996 | Oku et al. | ............... 514/311 |
| 5,786,365 | | 7/1998 | Heitsch et al. | ......................... 514/311 |
| 5,859,025 | * | 1/1999 | Wagner et al. | ....................... 514/311 |
| 5,952,346 | * | 9/1999 | Heitsch et al. | ......................... 514/311 |

FOREIGN PATENT DOCUMENTS

| 622361 | 11/1994 | (EP) . |
| 0 796 848 A1 | 9/1997 | (EP) . |
| 0 808 628 A2 | 11/1997 | (EP) . |
| WO96/13485 | 5/1996 | (WO) . |
| WO96/40639 | 12/1996 | (WO) . |
| WO 97/07115 | * | 2/1997 | (WO) . |
| WO 97/11069 | * | 3/1997 | (WO) . |

OTHER PUBLICATIONS

STN printout for WO 96/13485, May 1996*
STN printout for US 5,563,162, Oct. 1996.*
Cecil et al., Textbook of Medicine, vol. 2, pp. 1992–1996.*
CAPLUS printout for WO 97/07115, 1997.*
Gordon W. Gribble, et al., "Reactions of Sodium Borohydride in Acidic Media: III. Reduction and Alkylation of Quinoline and Isoquinoline with Carboxylic Acids," *Synthesis*, vol. 10 (1975), pp. 650–652.
Gabriele Wiemer, et al., "Ramiprilat Enhances Endothelial Autacoid Formation by Inhibiting Breakdown of Endothelium–Derived Bradykinin," *Hypertension*, vol. 18, No. 4 (1991), pp. 558–563.
K. Wirth, et al., "Hoe 140 A New Potent and Long Acting Bradykinin–Antagonist: In Vivo Studies," *Br. J. Pharmacol*, vol. 102 (1991), pp. 774–777.
M. Bickel, et al., "Beneficial Effects of Inhibitors of Prolyl 4–Hydroxylase in $CCl_4$–induced Fibrosis of the Liver in Rats," *Journal of Hepatology*, vol. 13 (Suppl. 3) (1991), S26–S34.
John M. Schaus, et al., "Synthesis of the Dopamine Agonist (–)–Quinpirole," *Synthetic Communications*, vol. 20, No. 22 (1990), pp. 3553–3562.
Von Heinz Fiedler, "Notiz über die Verwendung von Polyphosphorsäure ei der Reaktion Nach Döbner v. Miller," *J. Parkt. Chemie*, vol. 13 (1961), pp. 86–89.
Robert B. Innis, et al., "[$^3$H]Bradykinin Receptor Binding In Mammalian Tissue Membranes," *Proc. National Academy of Science*, USA, vol. 78, No. 4 (1981), pp. 2630–2634.
R.A. Raphael et al., *J. Chem. Soc. Perkin Trans. I*, (1988), pp. 1823–1828.

* cited by examiner

Primary Examiner—Mukund J. Shah
Assistant Examiner—Brenda Coleman
(74) Attorney, Agent, or Firm—Finnegan, Henderson, Farabow, Garrett & Dunner, L.L.P.

(57) ABSTRACT

Benzyloxy-substituted, fused N-heterocycles, because of their ability to act as bradykinin receptor antagonists, have been found to be useful as therapeutics for the treatment and prevention of liver cirrhosis or Alzheimer's disease. This application describes such compounds, as well as processes for their preparation and use. The compounds according to this invention include compounds of formula (I)

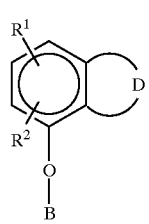

(I)

in which B, D, $R^1$, and $R^2$ have the meanings indicated herein.

22 Claims, No Drawings

BENZYLOXY-SUBSTITUTED, FUSED N-HETEROCYCLES, PROCESSES FOR THEIR PREPARATION, AND THEIR USE AS BRADYKININ RECEPTOR ANTAGONISTS

This application claims priority benefits under 35 U.S.C. § 119 based on German Patent Appln. No. 19712960.9, filed in Germany on Mar. 27, 1997.

BACKGROUND AND DESCRIPTION OF THE INVENTION

EP-A-622 361, WO 96-13485, and WO 96-40639, and the earlier priority, non-laid-open patent applications P 19610784.9 and P 19609827.0, disclose benzyloxy-substituted, fused N-heterocycles and their use as bradykinin antagonists.

The present invention relates to novel benzyloxy-substituted, fused N-heterocycles having high affinity for the bradykinin $B_2$ receptor and improved pharmacokinetics.

The compounds according to the invention are described by formula (I)

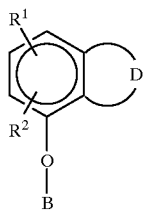

(I)

in which the symbols have the following meanings:

D is a radical of formula (II) or (III):

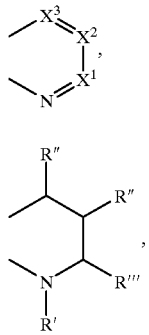

(II)

(III)

wherein:
$X^1$ is N or —C—$R^6$;
$X^2$ is N or —C—$R^7$; and
$X^3$ is N or —C—$R^8$;

B is a radical of formula (VIII):

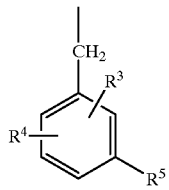

(VIII)

$R^1$ and $R^2$, which may be identical or different, are
1. hydrogen,
2. halogen, or
3. ($C_1$–$C_3$)-alkyl;

$R^3$ and $R^4$, which may be identical or different, are
1. hydrogen,
2. halogen,
3. cyano,
4. ($C_1$–$C_3$)-alkyl,
5. —O—($C_1$–$C_3$)-alkyl,
6. —S—($C_1$–$C_3$)-alkyl,
   wherein, in the radicals identified under 4, 5, and 6 above, 1 to 5 of the hydrogen atoms in the alkyl groups can be replaced by halogen atoms,
7. —OH,
8. tetrazolyl,
9. —CONHR$^9$, or
10. —COOR$^9$;

$R^5$ is
1. nitro,
2. amino,
3. a radical of formula (IV)

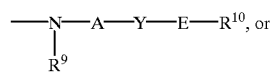

(IV)

4. a radical of formula (V)

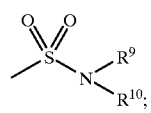

(V)

$R^6$, $R^8$, and R''', which may be identical or different, are
1. hydrogen,
2. halogen,
3. ($C_1$–$C_4$)-alkyl,
4. ($C_1$–$C_4$)-alkoxy,
5. amino,
6. ($C_1$–$C_4$)-alkylamino,
7. hydroxyl,
8. ($C_6$–$C_{12}$)-aryl,
9. ($C_6$–$C_{12}$)-aryl-($C_1$–$C_4$)-alkandiyl, or
10. —CO$_2$R$^9$;

$R^7$, R', and R'', which may be identical or different, are
1. hydrogen, or
2. ($C_1$–$C_4$)-alkyl,
wherein each R'' in formula (III) may be identical or different;

$R^9$ is
1. hydrogen,
2. $(C_1-C_4)$-alkyl,
3. $(C_2-C_5)$-alkenyl, or
4. $(C_6-C_{12})$-aryl-$(C_1-C_3)$-alkandiyl;

A is a bivalent radical of an aminocarboxylic acid, such as methionine, alanine, phenylalanine, tyrosine, o-methylthyrosine, β-(2-thienyl)alanine, glycine, cyclohexylalanine, leucine, isoleucine, valine, norleucine, phenylglycine, serine, cysteine, aminopropionic acid, or aminobutyric acid;

Y is

1.

2.

3.

E is
1. $(C_2-C_5)$-alkenediyl,
2. $(C_1-C_7)$-alkanediyl,
3. $(C_3-C_{10})$-cycloalkanediyl, or
4. —$(CH_2)_m$—$T_o$—$(CH_2)_n$—, wherein m, n, and o are defined such that —$(CH_2)_m$—$T_o$—$(CH_2)_n$— is not a $(C_1-C_7)$-alkanediyl,
   wherein the radicals, identified under 1–4 above, optionally, can be substituted by one or more groups, such as —O—$R^{12}$, —$NO_2$, —CN, —$CO_2R^9$, —$NR^{13}R^{14}$, —$SO_3R^{12}$, —$SO_2NR^{13}R^{14}$ or —$CONR^{13}R^{14}$;

T is
1. O,
2. S, or
3. $NR^{15}$;

m and n, which may be identical or different, are each an integer from 0–6;

o is an integer 0 or 1;

$R^{10}$ is
1. hydrogen,
2. $(C_1-C_5)$-alkyl,
3. $(C_6-C_{10})$-aryl,
4. $(C_1-C_3)$-alkandiyl-$(C_6-C_{10})$-aryl-, or
5. a heteroaryl group,
   wherein radicals 3, 4, and 5 above can optionally be substituted by one or more groups, such as halogen, —CN, —$NO_2$, $(C_1-C_5)$-alkylthio, —$NR^{13}R^{14}$, —$NR^{13}CO$—$R^{16}$, —$CO_2R^9$, —$SO_3R^{12}$, —$SO_2NR^{13}R^{14}$, —$OR^{12}$, $(C_1-C_6)$-alkyl, $(C_6-C_{10})$-aryl, $(C_2-C_5)$-alkenyl, and $(C_1-C_5)$-alkoxy, and wherein the last four radicals (i.e., the $(C_1-C_6)$-alkyl, $(C_6-C_{10})$-aryl, $(C_2-C_5)$-alkenyl, and $(C_1-C_5)$-alkoxy radicals) can optionally be partially or completely substituted by halogen;

$R^{12}$ and $R^{13}$, which may be identical or different, are 1. hydrogen,
2. $(C_1-C_5)$-alkyl,
3. $(C_2-C_5)$-alkenyl,
4. $(C_6-C_{12})$-aryl,
5. $(C_6-C_{12})$-aryl-$(C_1-C_5)$-alkandiyl,
6. $(C_3-C_{10})$-cycloalkyl,
7. $(C_3-C_{10})$-cycloalkyl-$(C_1-C_2)$-alkandiyl,
8. —C(O)—O—$(C_1-C_5)$-alkyl, or
9. —C(O)NH—$(C_1-C_5)$-alkyl;

$R^{14}$ is
1. hydrogen,
2. —C(O)—O—$(C_1-C_4)$-alkyl, or
3. —C(O)—O—$(C_1-C_3)$-alkyl-$(C_6-C_{10})$-aryl;

$R^{15}$ is
1. hydrogen,
2. —C(O)—$(C_1-C_3)$-alkyl, or
3. $(C_1-C_3)$-alkyl; and $R^{16}$ is
1. $(C_1-C_3)$-alkyl,
2. $(C_6-C_{12})$-aryl, or
3. a heteroaryl group,
   wherein these radicals can optionally be substituted by one or more groups, such as halogen, —CN, —$NO_2$, —$NR^{13}R^{14}$, and —$CO_2R^9$;

and their physiologically tolerable salts;

with the proviso that in the case of compounds of formula (I) in which D is a radical of formula (II), $R^3$ and $R^4$ are not simultaneously halogen, $(C_1-C_3)$-alkyl, and/or —O—$(C_1-C_3)$-alkyl, or $R^3$ and $R^4$ are not hydrogen in combination with halogen, $(C_1-C_3)$-alkyl, or —O—$(C_1-C_3)$-alkyl; excluded from these are α. compounds of formula (I) in which D is a radical of formula (II) and $R^5$ is a radical of formula (IV), wherein $R^{10}$ is a heteroaryl group or a radical of formula (VI)

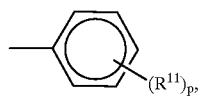

(VI)

wherein p is an integer from 1 to 3; and
$R^{11}$ is
1. $(C_1-C_5)$-alkyl, wherein the hydrogen atoms are partially or completely replaced by fluorine or chlorine, or
2. $(C_1-C_5)$-alkoxy, wherein the hydrogen atoms are partially or completely replaced by fluorine or chlorine;

for which, for its part, the proviso applies that when $R^{10}$ has the formula (VI), $R^3$ and $R^4$ are not identically or differently hydrogen and halogen; and β. compounds of formula (I) in which D is a radical of formula (II) and $R^5$ is a radical of formula (V), for which, for its part, the proviso applies that $R^3$ and $R^4$ are not halogen.

To summarize, this invention relates to compounds according to formula (I) (and their physiologically tolerable salts), as defined above. Specifically, the invention includes the compounds and salts according to formula (I), except, the compounds and salts according to provisos (A) and (B) below are not included within the scope of the invention:

(A) compounds and salts of formula (I) in which D is a radical of formula (II), and $R^3$ and $R^4$ are simultaneously halogen, $(C_1-C_3)$-alkyl, and/or —O—$(C_1-C_3)$-alkyl; and (B) compounds and salts of formula (I) in which D is a radical of formula (II), and $R^3$ and $R^4$ are hydrogen in combination with halogen, $(C_1-C_3)$-alkyl, or —O—$(C_1-C_3)$-alkyl.

There are exceptions to the provisos (A) and (B) above. In particular, of the compounds and salts according to (A) and (B) which would be excluded from the scope of this invention by the terms of provisos (A) and (B), the following compounds and salts defined in (α) and (β) are included within the scope of this invention:

(α) compounds and salts of formula (I) in which D is a radical of formula (II) and $R^5$ is a radical of formula (IV), where $R^{10}$ is a heteroaryl group or a radical of formula (VI)

wherein p is an integer from 1 to 3, and $R^{11}$ is: (a) a $(C_1-C_5)$-alkyl, wherein the hydrogen atoms are partially or completely replaced by fluorine or chlorine, or (b) a $(C_1-C_5)$-alkoxy, wherein the hydrogen atoms are partially or completely replaced by fluorine or chlorine; and (β) compounds and salts of formula (I) in which D is a radical of formula (II) and $R^5$ is a radical of formula (V). Of the compounds and salts included within the scope of the invention by proviso α above, however, the following compounds and salts are excluded from the scope of the invention: (i) compounds and salts where $R^{10}$ has the formula (VI) and $R^3$ and $R^4$ are, identically or differently, hydrogen or halogen. Additionally, of the compounds and salts included within the scope of the invention by proviso β above, the following compounds and salts are excluded from the scope of the invention: (ii) compounds and salts where $R^3$ and $R^4$ are halogen.

Alkyl and alkenyl groups included in the compounds according to formula (I) can be straight-chain or branched. The same applies to radicals derived therefrom, such as, for example, alkoxy groups.

"Alkenyl" represents mono- or polyunsaturated radicals, such as 1,4-butadienyl and butenyl.

"Cycloalkyl" represents mono- or bicyclic radicals, such as cyclopropyl, cyclopentyl, cyclohexyl, and bicyclononyl. Likewise, "cycloalkenyl" represents mono- or bicyclic radicals, at least one of which includes a mono- or polyunsaturation.

A "$(C_6-C_{12})$-aryl" is, for example, phenyl, naphthyl, or biphenylyl, and preferably phenyl. The same also applies to radicals derived from aryl groups, e.g., in arylalkyl groups, the "aryl" represents, for example, phenyl, naphthyl, or biphenylyl, and preferably phenyl.

"Halogen" (or "Hal") represents fluorine, chlorine, bromine, or iodine, wherein chlorine or fluorine is preferred.

A "heteroaryl group" means a radical of monocyclic or bicyclic aromatic 5- and/or 6-membered ring systems which are derived from cyclopentadienyl, phenyl, indenyl, or naphthyl, wherein one or more CH-groups are replaced by N, NH, S, and/or O, and whereby the aromatic ring system is retained. In addition, one or both atoms of the condensation site of bicyclic radicals can also be nitrogen atoms, such as in indolizinyl. Generally, heteroaryl groups are ring structures containing five to ten ring atoms, one to nine of which are carbon atoms.

Examples of suitable heteroaryl groups include furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl, cinnolinyl, benzopyranonyl, coumarinyl, pyranonyl, and furandionyl.

All of the above-mentioned definitions also apply when these terms are used in connection with the corresponding bivalent radicals.

"Physiologically tolerable salts" of compounds of formula (I) are understood as meaning both their inorganic and organic salts, as are described in Remington's Pharmaceutical Sciences (A. R. Gennard Editor, Mack Publishing Co., Easton Pa., 17th Edition, page 1418 (1985). On account of their physiological and chemical stability and their solubility, acidic groups, such as, inter alia, sodium, potassium, calcium, and ammonium salts, are preferred; for basic groups, inter alia, salts of hydrochloric acid, sulfuric acid, or phosphoric acid, or of carboxylic acids or sulfonic acids, such as, acetic acid, citric acid, benzoic acid, maleic acid, fumaric acid, tartaric acid, and p-toluenesulfonic acid, are preferred.

Preferred compounds of formula (I) are those in which the symbols have the following meanings:

$X^1$ is —C—$R^6$;
$X^2$ is —C—$R^7$;
$X^3$ is —C—$R^8$;
$R^1$ and $R^2$, which may be identical or different, are
  1. hydrogen, or
  2. methyl or ethyl;
R', R'", $R^6$, $R^7$, and $R^8$, which may be identical or different, are
  1. hydrogen, or
  2. $(C_1-C_4)$-alkyl;
R" is hydrogen;
A is the bivalent radical of the amino acid glycine or alanine;

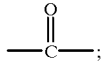

Y is
E is
  1. $(C_2-C_5)$-alkenediyl,
  2. $(C_1-C_7)$-alkanediyl, or
  3. —$(CH_2)_m$—$T_o$—$(CH_2)_n$—, wherein m, n, and o are defined such that —$(CH_2)_m$—$T_o$—$(CH_2)_n$— is not a $(C_1-C_7)$-alkanediyl,
    wherein the radicals identified under 1–3 above are optionally substituted by a group selected from —$OR^{12}$, —$NO_2$, —CN, —$CO_2R^9$, —$NR^{13}R^{14}$, —$SO_3R^{12}$, —$SO_2NR^{13}R^{14}$, or —$CONR^{13}R^{14}$;
T is
  1. O, or
  2. NH;
m and n, which may be identical or different, are each an integer from 0–3; p is an integer 1 or 2;
$R^{11}$ is
  1. —$CF_3$, or
  2. —$OCF_3$;

$R^{12}$ and $R^{13}$, which may be identical or different, are
1. hydrogen,
2. $(C_1–C_5)$-alkyl,
3. $(C6–C_{12})$-aryl, or
4. $(C_6–C_{12})$-aryl-$(C_1–C_3)$-alkandiyl;

$R^{15}$ is
1. hydrogen, or
2. methyl or ethyl;

and their physiologically tolerable salts;
and the other radicals, variables, and provisos are as defined above for formula (I).

Particularly preferred compounds of formula (I) are those in which the symbols have the following meanings:

D is a radical of formula (II) or (III);
B is a radical of formula (IX)

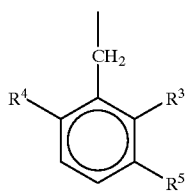

(IX)

$X^1$ is —C—CH$_3$;
$X^2$ is —C—H;
$X^3$ is —C—H;
R' is methyl;
R'' is hydrogen;
R''' is methyl;
$R^1$ and $R^2$ are each hydrogen;
$R^3$ and $R^4$, which may be identical or different, are
1. chlorine,
2. cyano,
3. methyl,
4. —O—methyl,
5. —S—methyl,
6. —OH,
7. tetrazolyl, or
8. —CONH$_2$;

$R^5$ is.
1. nitro,
2. amino,
3. a radical of formula (X)

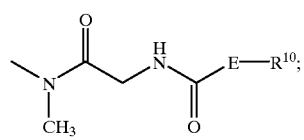

(X)

4. a radical of formula (V)

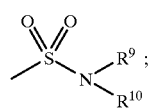

(V)

$R^9$ is
1. hydrogen,
2. methyl, ethyl, n-propyl, i-propyl, n-butyl, or i-butyl, or
3. benzyl;

E is
1. $(C_2–C_5)$-alkenediyl,
2. $(C_1–C_7)$-alkanediyl, or
3. —$(CH_2)_m$—$T_o$—$(CH_2)_n$—, wherein m, n, and o are defined such that —$(CH_2)_m$—$T_o$—$(CH_2)_n$— is not a $(C_1–C_7)$-alkanediyl group, wherein the radicals identified under 1–3 above are optionally substituted by a group selected from —OR$^{12}$, —CO$_2$R$^9$, —NR$^{13}$R$^{14}$, or —CONR$^{13}$R$^{14}$;

T is
1. O, or
2. NH;

m and n, which may be identical or different, are each a number from 0 to 3; o is a number 0 or 1;

$R_{10}$ is
1. hydrogen,
2. $(C_1–C_5)$-alkyl,
3. phenyl,
4. benzyl, or
5. a heteroaryl group containing 4 to 7 carbon atoms in the ring structure, preferably furyl or pyridyl,
wherein 3, 4, and 5 above can optionally be substituted by one or two groups selected from $(C_1–C_5)$-alkyl, $(C_1–C_5)$-alkoxy, —CF$_3$, —OCF$_3$, —NR$^{13}$R$^{14}$, —NR$^{13}$CO—R$^{16}$, and —CO$_2$R$^9$;

$R^{11}$ is
1. —CF$_3$, or
2. —OCF$_3$;

$R^{12}$ and $R^{13}$, which may be identical or different, are
1. hydrogen,
2. methyl, ethyl,
3. phenyl, or
4. benzyl;

$R^{14}$ is
1. hydrogen,
2. —C(O)—O—C—(CH$_3$)$_3$, or
3. —C(O)—O—CH$_2$-phenyl; and $R^{16}$ is
1. methyl or ethyl,
2. phenyl, or
3. a heteroaryl group, wherein the ring structure contains 4 to 7 carbon atoms,
wherein these radicals can optionally be substituted by one or two groups selected from —NR$^{13}$R$^{14}$ or —CO$_2$R$^9$;

and their physiologically tolerable salts;
with the proviso that in the case of compounds of formula (I) in which D is a radical of formula (II), $R^3$ and $R^4$ are not simultaneously chlorine, methyl, and/or O-methyl; excluded from these are α. compounds of formula (I) in which D is a radical of formula (II) and $R^5$ is a radical of formula (X) wherein $R^{10}$ is a heteroaryl group containing 4 to 7 carbon atoms in the ring structure or a radical of formula (VII)

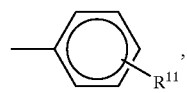

(VII)

for which, for its part, the proviso applies that in the case of compounds of formula (I) in which the radical $R^{10}$ has the formula (VII), $R^3$ and $R^4$ are not chlorine; and β. compounds of formula (I) in which D is a radical of formula (II) and $R^5$ is a radical of formula (V); for which, for its part, the proviso applies that $R^3$ and $R^4$ are not chlorine.

Very particularly preferred compounds of formula (I) are those in which D is formula (II) and the other radicals, variables, and provisos are as defined above for formula (I).

The invention additionally relates to processes for the preparation of compounds of formula (I). The first method is described below.

Method I:

a) reacting a compound of formula (XI)

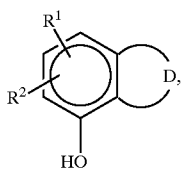
(XI)

in which $R^1$, $R^2$, and D are as defined above for formula (I), in the presence of metal hydrides, such as lithium, potassium, or sodium hydride, or alkali metal carbonates, such as $Na_2CO_3$, $K_2CO_3$, or $Cs_2CO_3$, in an inert solvent, such as DMF or DMSO, at temperatures from 0° C. to 60° C., preferably at room temperature, with a compound of formula (XII)

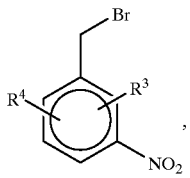
(XII)

in which $R^3$ and $R^4$ are as defined above in formula (I), to give a compound of formula (XIII)

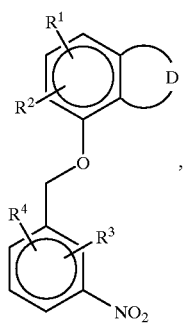
(XIII)

in which $R^1$, $R^2$, $R^3$, $R^4$, and D are as defined above;

b) reducing the compound of formula (XIII) with the aid of transition metal halides, preferably $SnCl_2$ and $FeCl_3$, to a compound of formula (XIV)

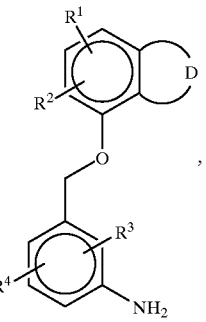
(XIV)

in which $R^1$, $R^2$, $R^3$, $R^4$, and D are as defined above;

c) reacting the compound of formula (XIV) with activated, suitably protected aminocarboxylic acid derivatives of A ("A-Prot"), preferably the acid chlorides of the phthaloyl-protected aminocarboxylic acid derivatives of A, in inert solvents, such as $CH_2Cl_2$ or N-methylpyrrolidone, if appropriate by addition of DMAP, in the presence of a base, such as pyridine, and thus obtaining a compound of formula (XV)

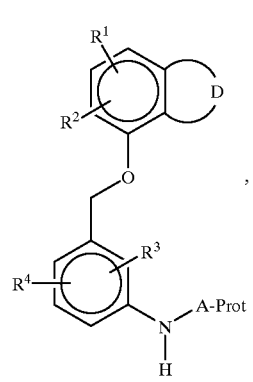
(XV)

in which A, $R^1$, $R^2$, $R^3$, $R^4$, and D are as defined above, and Prot is an amino-protective group, such as those described in T. W. Greene, "Protective Groups in Organic Synthesis", Verlag John Wiley, 2nd Edition 1991(suitable protective groups include, e.g., phthaloyl, benzyl, or paramethoxybenzyl);

d) reacting the compound of formula (XV), after action of alkali metal hydrides, alkali metal carbonates or alcoholates, in inert solvents, preferably DMF or N-methylpyrrolidone, followed by a treatment with $R^9X$, wherein $R^9$ is as defined above in formula (I) and X is a leaving group, e.g., halogen, mesylate, or tosylate, a compound of formula (XVI) being obtained (XVI)

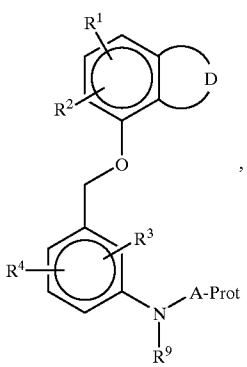

in which $R^1$, $R^2$, $R^3$, $R^4$, $R^9$, D, and A are as defined above and Prot is as defined in formula (XV); and e) converting the compound of formula (XVI) under suitable conditions into a compound of formula (XVII) shown below. This can be accomplished, for example, by hydrazinolysis in ethanol, in the case where a phthaloyl group is present as a protective group Prot, at a temperature from 20° C. up to the boiling point, to thereby provide the compound of formula (XVII)

(XVII)

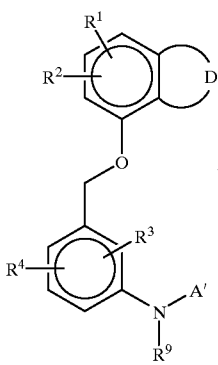

in which $R^1$, $R^2$, $R^3$, $R^4$, $R^9$, and D are as defined above, and A' is a radical of an aminocarboxylic acid.

The compound according to formula (XVII) is then reacted under suitable conditions to produce a compound of formula (I). Such conditions include:

f1) reacting the compound of formula (XVII) with activated carboxylic acid and sulfonic acid derivatives $R^{10}$—E—Y—OH, in which $R^{10}$, E, and Y are as defined above in formula (I), in conventional organic solvents, such as $CH_2Cl_2$, dioxane, THF, or DMF, in the presence of an inorganic or organic base at a temperature from 0° C. to reflux, to give a compound of formula (I), in which $R^1$, $R^2$, $R^3$, $R^4$, $R^9$, $R^{10}$, A, D, and E have the above-mentioned meanings, B is a radical of formula (VIII), and $R^5$ is a radical of formula IV, or f2) reacting a compound of formula (XVII) with an amine $R^{10}$—E—$NH_2$, or an alcohol $R^{10}$—E—OH, preferably at a temperature from 0° C. to room temperature, in inert solvents, such as dichloromethane or dimethoxyethane, to give a compound of formula (I), in which $R^1$, $R^2$, $R^3$, $R^4$, $R^9$, $R^{10}$, A, D, and E have the above-mentioned meanings, B is a radical of formula (VII), and $R^5$ is a radical of formula IV, where first, however, the compounds of formula (XVII) or the amine or the alcohol are allowed to react with a doubly activated carbonyl compound to form the urea or urethane group, e.g., with carbodiimides, phosgene, or chlorocarbonic acid esters, preferably phosgene and carbonyldiimidazole, or f3) reacting a compound of formula (XVII) with an appropriate isocyanate or isothiocyanate, preferably at a temperature from 0° C. to room temperature, in inert solvents, preferably dichloromethane or dimethoxyethane, to give a compound of formula (I), in which $R^1$, $R^2$, $R^3$, $R^4$, $R^9$, $R^{10}$, A, D, and E have the above-mentioned meanings, B is a radical of formula (VII), and $R^5$ is a radical of formula IV. The following is the optional final step:

g) optionally, converting the obtained compounds of formula (I), according to known methods, into their physiologically tolerable salts;

A second process for making the compounds according to the invention is described below.

Method II:

a) reacting a compound of formula (XI)

(XI)

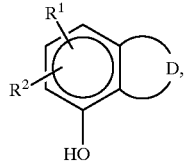

in which $R^1$, $R^2$, and D are as defined above for formula (I), in the presence of metal hydrides, such as lithium, potassium, or sodium hydride, or alkali metal carbonates, such as $Na_2CO_3$, $K_2CO_3$, or $Cs_2CO_3$, in an inert solvent, such as DMF or DMSO, at a temperature from 0° C. to 60° C., preferably at 20 to 30° C., with a compound of formula (XVIII)

(XVIII)

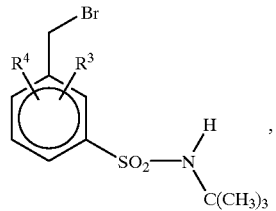

in which $R^3$ and $R^4$ are as defined above in formula (I), to give a compound according to formula (XIX)

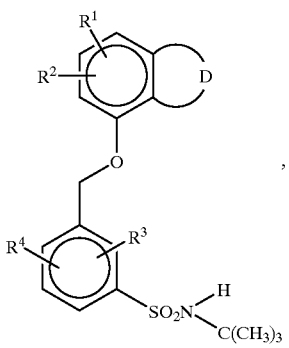

(XIX)

in which $R^1$, $R^2$, $R^3$, $R^4$, and D are as defined above;

b) reacting the compound of formula (XIX) in the presence of metal hydrides, such as sodium hydride, in inert solvents such as DMF, THF, or DMSO, with alkyl or aryl halides $R^9$-Hal, wherein $R^9$ is alkyl or aryl as defined above and Hal is preferably iodide, at a temperature from 0° C. to 40° C., to produce a compound according to formula (XX)

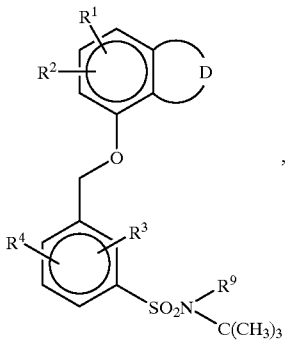

(XX)

in which $R^1$, $R^2$, $R^3$, $R^4$, $R^9$, and D are as defined above;

c) treating the compound of formula (XX), first with an excess of acid, preferably trifluoroacetic acid, in the presence of a cation scavenger, such as anisole, for 4 to 24 hours at a temperature from 20° C. to 60° C. in an inert solvent, such as $CH_2Cl_2$, and then reacting the compound obtained in the presence of an inorganic or organic base, such as $Cs_2CO_3$ or NaH, with halides of formula Hal-$R^{10}$, in which $R^{10}$ has the meaning indicated above in formula (I), excluding hydrogen, to give compounds of formula (I), in which $R^1$, $R^2$, $R^3$, $R^4$, $R^9$, D, and $R^{10}$ have the above-mentioned meanings, B is a radical of formula (VIII), and $R^5$ is a radical of formula (V); and d) optionally converting the compounds of formula (I) thus obtained into their physiologically tolerable salts.

Processes for the preparation of the compounds of formula (XI) in which D is a radical of formula (VI) are known, inter alia, from H. Fiedler, J. Prakt. Chemie, Vol. 13, 1961, 86 ff.

Processes for the preparation of the compounds of formula (XI) in which D is a radical of formula (VII) are known, inter alia, from G. Gribble et al., Synthesis 10, (1975), pp. 650–652 and J. M. Schaus et al., Synth. Commun. 20, (1990), 3553–3562.

The conversion to the bromomethyl compound of formula (XII) or (XVIII) is carried out by reaction of the corresponding methyl derivative with N-bromosuccinimide or 1,3-dibromo-5,5-dimethyl hydantoin in inert solvents, preferably chlorobenzene or cyclohexane, at temperatures from 60° C. up to the boiling point.

The replacement of chlorine by alkoxy or the corresponding S-alkylene is carried out by reaction with the corresponding alcoholates or thiolates, preferably their alkali metal or alkaline earth metal salts, in inert solvents between 0° C. and 60° C., preferably between 0° C. and room temperature.

The cyano derivatives are prepared by substitution of chlorine by cyano by action of cyanides, preferably copper cyanide, in inert high-boiling solvents, such as DMF or N-methylpyrrolidone, at their boiling point.

The amide compounds result from the corresponding nitrile compounds by treatment with alkaline $H_2O_2$ solution in alcoholic solution at temperatures from room temperature up to the boiling point.

The phenolic compounds result from the treatment of the corresponding alkoxy derivatives with Lewis acids, such as boron tribromide, in inert solvents at temperatures between 0° C. and room temperature.

The methyl derivative of the compound of formula (XVIII) results from reaction of the corresponding sulfochloride derivative with t-butylamine in $CH_2Cl_2$ at room temperature.

Additionally, it is noted that, inter alia, Examples 1a, 11a, 13b, and 16a below describe production of compounds of formula (XII), and Example 26 below describes production of a compound of formula XVIII.

Activated acid derivatives used in Method I, step f1, are acid chlorides, acid anhydrides, and active esters, e.g., carboxylic and sulfonic acid chlorides and bromides, mixed anhydrides, symmetrical anhydrides, p-nitrophenyl esters, and hydroxysuccinimide esters. The choice of one of these activated derivatives is dependent on the acyl or sulfonyl group to be introduced. In the case of the free carboxylic acids, the reaction is carried out in the presence of the condensing reagents used in peptide chemistry (see, for example, Houben-Weyl, Methoden der Organischen Chemie [Methods of Organic Chemistry], Vol. 15/2, Georg Thieme Verlag, Stuttgart, 1974), in particular carbodiimides such as N,N'-dicyclohexylcarbodiimide, N,N'-diisopropylcarbodiimide and N-ethyl-N'-(3-dimethylaminopropyl)carbodiimide or chromium salts such as O-[cyano(ethoxy-carbonyl)methylenamino]-1,1,3,3-tetramethyluronium tetrafluoroborate (TOTU) and O-benzotriazol-1-yl-N,N,N',N'-tetramethyluronium hexafluorophosphate (MBTU).

Individually or in combination, the compounds of formula (I) according to the invention have a bradykinin-antagonistic action which can be tested in various models (see the Handbook of Exp. Pharmacol., Vol. 25, Springer Verlag, 1970, pp. 53–55), for example, on the isolated rat uterus, on the guinea-pig ileum, on the isolated pulmonary artery of the guinea-pig, or on the jugular vein of the rabbit.

The effects of the compounds of formula (I) on bradykinin-induced bronchoconstriction and on carrageenin-induced paw edema can be determined in a manner analogous to the procedure described in the Br. J. Pharmacol., 102, 774–777 (1991).

The natriuretic and diuretic effect of the compounds of formula (I), including the compounds excluded therefrom under β, in chronic fibrogenetic liver disorders and acute liver disorders can be determined in the $CCl_4$-induced liver fibrosis model in the rat (see Bickel et al., *J. Hepatol.* (1991), 13 (Suppl. 3), S26–33).

The action of the compounds of formula (I), including the compounds excluded therefrom under β, on the cGMP production stimulated by the Alzheimer protein amyloid (β/A4) in isolated endothelial cells can be tested in the following manner:

Test Systems:
Bovine aorta endothelial cell cultures and microvascular coronary endothelial cell cultures Method:
Determination of the effect of bradykinin receptor antagonists of formula (I) on the production of cGMP ("cyclic guanosine monophosphate") stimulated by administration of 1 μmol/l of the Alzheimer protein β/A4 in endothelial cell cultures.

It has been adequately shown that endothelial cells are a suitable test system for the detection of an action and release of bradykinin (see G. Wiemer et al., *Hypertension*, 1991; 18: 558–563). In endothelial cells, bradykinin leads to an increase in the production of cGMP, which is determined by means of a radioimmunoassay. An increase in the formation of cGMP by bradykinin is an indicator of a release of NO (nitrogen monoxide) from endothelial cells.

Result:
The simultaneous incubation of the above-mentioned cell cultures with the compounds of formula (I), including the compounds excluded therefrom under β, in concentrations of 10 nM/l up to 10 μM/l, prevents the stimulation of the production of cGMP induced by the β/A4 protein.

Assessment:
The experiment carried out indicates that the action of the Alzheimer protein β/A4 on the production of cGMP is mediated via binding of bradykinin to its cell receptors.

Endothelial cell cultures are used here as an indicator of an action of β/A4 which is mediated via bradykinin. The endothelial cells in this case, however, are not only the indicator system for an action via bradykinin receptors, but also the effector organ in Alzheimer's disease. Endothelial cells are constituents of the blood vessels and form these. The blood vessels themselves are severely affected by deposits of the Alzheimer protein amyloid (β/A4) in Alzheimer's disease in addition to neuronal tissue. Endothelial cells are responsible for an increase in the permeability of the blood-brain barrier caused by bradykinin.

The determination of the affinity of the compounds of formula (I) for the bradykinin $\beta_2$ receptor was carried out on membrane preparations of the guinea-pig ileum (see R. B. Innis et al., *Proc. Natl. Acad. Sci. USA*, 17 (1981) 2630) according to the following procedure:

1. Ligand: $^3$H-BRADYKININ (from NEN Du Pont)
2. Buffer mixtures:
    a) TES buffer:
        25 mM TES (SIGMA, Order No.: T-4152)
        1 mM 1,10-phenanthroline (SIGMA; Order No.: P-9375)
    b) Incubation buffer:
        25 mM TES (SIGMA; Order No.: T-4152)
        1 mM 1,10-phenanthroline (SIGMA; Order No.: P-9375)
        0.1% albumin, bovine (SIGMA; Order No.: A-7906)
        140 μg/ml bacitracin (SIGMA; Order No.: B-0125)
        1 mM dithiothreitol (SIGMA; Order No.: D-0632)
        1 μM captopril-1-[(2S)-3-mercapto-2-methylpropionyl]-L-proline Both buffers are adjusted to pH 6.8 using 5 molar NaOH.

3. Membrane preparation:
Guinea-pig ilea are grossly freed from intestinal contents by careful brushing and cleaned in 0.9% strength NaCl solution.

The pieces of ilea about 2 cm long are transferred to ice-cold TES buffer (about 1 g/10 ml) and homogenized in an ice bath for about 30 sec. using an Ultraturrax. The homogenate is then filtered through three layers of gauze, and the filtrate is centrifuged at 50,000 g/10 minutes.

The supernatant is discarded, and the pellet is rehomogenized in the same volume of TES buffer and centrifuged again at 50,000 g/10 minutes. The pellet is rehomogenized in incubation buffer (about 1 g/5 ml) and frozen at −70° C. in cryotubes in 2 ml portions.

The protein concentration of the finished membrane suspension is determined according to LOWRY and should be about 15 μg/100 μl.

4. Binding test:
All incubations are carried out at room temperature for 60 minutes on microtiter plates (96×300 μl) in a 200 μl volume. All mixtures are in incubation buffer. To this end, 50 μl of the radioligand, 50 μl of the preparation to be tested, and 100 μl of the membrane suspension are pipetted into the hollows of the microtiter plate in succession.

a) Saturation experiments (hot saturation):
Preparation of the $^3$H-bradykinin solution: for the saturation experiments, the concentrations 0.05, 0.1, 0.2, 0.4, 0.6, 0.8, 1.0, 1.5, 2.0, 2.5, and 3.0 nmol/l are employed, which correspond to 0.05 to 3.0 pmol/ml. After the preparation of the appropriate dilutions, 50 μl each are initially introduced per sample.

Nonspecific binding: for each concentration of the radioactive ligand, the nonspecific binding must be determined. This can be achieved by addition of a high concentration (1–100 μmol) of the unlabeled ligand, other antagonists or agonists of the bradykinin receptor. In this test, HOE 140 (10 μmol/l) is used. To this end, 1.862 mg are dissolved in 1 ml of dimethyl sulfoxide (DMSO), diluted 1:25 with incubation buffer, and 50 μl of this solution are added to the samples in the microtiter plate. The reaction is started by the addition of 100 μl of the membrane suspension.

b) Competition experiments ($IC_{50}$):
Here a fixed quantity of the radioactive ligand (0.25 to 0.3 nmol/l of $^3$H-bradykinin) and various concentrations of the unlabeled agonists or antagonists are employed.

50 μl of the preparations or standard to be tested in the concentrations $10^{-5}$ to $10^{-10}$ mol/l are added to 50 μl in each case of the $^3$H-bradykinin solution, and the reaction is started by addition of 100 μl of membrane suspension. Triplicate determinations also are carried out in this test, and three samples are incubated with 10 μmol/l of HOE 140 to determine the nonspecific binding.

The preparations to be tested for competition are completely dissolved in a concentration of 1 mmol/l in dimethyl sulfoxide (DMSO), and then further diluted with DMSO. This solution is then diluted 1:25 with incubation buffer.

After the incubation, the samples are filtered off in a Skatron cell harvester through a Whatmann GF/B filter paper strip previously moistened with 0.1% PEI (polyethylenimine) and washed with 10 ml of ice-cold TES buffer per sample. The still moist filters are punched out into mini-scintillation tubes, and these are filled with 3 ml of scintillator.

After a soaking time of about 12 hours, the samples are briefly shaken and measured in a beta-counter.

c) Screening:
In primary screening, in general only 1–2 concentrations of the test preparation ($10^{-5}$ and $10^{-6}$ mol/l) are employed.

If a displacement of the radioligand of 50% or more is detectable at the highest concentration, a complete analysis (competition experiment) is carried out using at least 8 concentrations.

4. Assessment:

Assessment is carried out by means of the LIGAND program package (McPherson, Minson & Rodbard, marketed by: Elsevier-BIOSOFT), which carries out the necessary calculations for the determination of $IC_{50}$ and $K_i$ values. This program moreover carries out graphic presentations of the saturation or displacement curves as well as the SCATCHARD plot, HILL plot, or HOFSTEE plot.

5. Test results

According to the above-mentioned procedure, the following $K_i$ values were determined for the compounds of Examples 1, 6, 9, 16, 20, and 24, as described below, as representative compounds of the described benzyloxy-substituted, fused N-heterocycles of formula (I):

| Example | $K_i$ [nM] |
|---------|-----------|
| 1 | 8.3 |
| 6 | 0.1 |
| 9 | 6.0 |
| 16 | 17.4 |
| 20 | 5.4 |
| 24 | 1.0 |

In addition, for the determination of the bradykinin-antagonistic action of the compounds of fomula (I), their effect on the bradykinin-induced contraction of the guinea-pig ileum can be measured according to the following protocol:

Guinea-pigs about 300 g in weight (Morioth strain, ♂ ♀) are killed by a blow to the neck and exsanguinated. The ileum is dissected out in a length of about 20 cm, rinsed with Tyrode solution (Record Syringe), and thus freed from the intestinal contents. It is then divided into sections 1.5 cm long. These are fixed in organ baths of 10 ml capacity, which are filled with Tyrode solution, and connected to extension-measuring strips (isometric contraction measurement). The preload is 1 g. The Tyrode solution is warmed to 37° C. in a water bath and bubbled through with compressed air. After an interval of 30 min, the experiment is begun. After recording the biological zero line, bradykinin in a final concentration of $4 \times 10^{-8}$ mol/l is added per organ bath, and the concentration is recorded. Rinsing with Tyrode solution is then carried out for three min., and after a break of 20 min., bradykinin is again added. The maximum of the contraction is achieved (control). Rinse again, break. The bradykinin antagonist is then added (action time 10 min.). Bradykinin is then again added, and the contraction then taking place is compared with that of the control. The experiment is recorded on a pen recorder.

Tyrode solution (mM):

| | |
|---|---|
| NaCl | 137 |
| Glucose | 5.05 |
| KCl | 2.68 |
| $NaHCO_3$ | 11.9 |
| $NaH_2PO_4$ | 0.47 |
| $MgCl_2 \times 2H_2O$ | 0.49 |
| $CaCl_2 \times 2H_2O$ | 0.68 |

Amplifier: TF6 V3 Fleck, Mainz
Pen recorder: Goerz Metrawatt SE 460, BBC
Bradykinin: Bachem Thus, the compounds of Examples 6 and 20, for example, have the following $IC_{50}$ values determined by the above procedure:

| Example | $IC_{50}$ |
|---------|-----------|
| 6 | $3.5 \times 10^{-7}$M |
| 20 | $5.6 \times 10^{-8}$M |

For the oral administration form or for application to the mucous membranes, the active compounds are mixed with additives customary for this purpose, such as excipients, stabilizers, or inert diluents, and are brought by means of customary methods into suitable administration forms, such as tablets; coated tablets; hard capsules; aqueous, alcoholic, or oily suspensions; or aqueous, alcoholic, or oily solutions. Inert carriers which can be used are, for example, gum arabic, magnesia, magnesium carbonate, potassium phosphate, lactose, glucose, magnesium stearyl fumarate, or starch, and in particular cornstarch. In this case, the preparation can be carried out both as dry and moist granules. Suitable oily excipients or solvents are, for example, vegetable or animal oils, such as sunflower oil and cod-liver oil.

A preparation for topical application can be present as an aqueous or oily solution, lotion, emulsion, or gel, ointment or fatty ointment or, if possible, in spray form, where adhesion can be improved, if appropriate, by addition of a polymer.

For the intranasal administration form, the compounds are mixed with additives customary for this purpose, such as stabilizers or inert diluents, and are brought by means of customary methods into suitable administration forms, such as aqueous, alcoholic, or oily suspensions or aqueous, alcoholic, or oily solutions. Chelating agents, ethylenediamine-N,N,N',N'-tetraacetic acid, citric acid, tartaric acid, or their salts can be added to aqueous intranasal preparations. The administration of the nasal solutions can be carried out by means of metered atomizers or as nasal drops having a viscosity-enhancing component or as nasal gels or nasal creams.

The compounds of formula (I) and their pharmacologically suitable salts are potent bradykinin antagonists. They can therefore be used for the treatment and/or the prevention of all pathological conditions which are mediated, caused or assisted by bradykinin and bradykinin-analogous peptides. This includes, inter alia, allergies, inflammations, autoimmune disorders, shock, pain, and, more especially, asthma, coughs, bronchitis, rhinitis, chronic obstructive pulmonary disorders, pneumonitis, septic shock, endotoxic shock, anaphylactic shock, disseminated intravascular coagulopathy, arthritis, rheumatism, osteoarthritis, lumbago, inflammation-induced bone resorption, conjunctivitis, iritis, headache, migraine, toothache, backache, cancer-related pain, postoperative pain, traumata (wounds, burns etc.), exanthema, erythema, edema, eczema, dermatitis, zoster, herpes, pruritus, psoriasis, lichen, inflammatory intestinal disorders, hepatitis, pancreatitis, gastritis, esophagitis, nutritional allergies, ulcers, irritable bowel, angina, cerebral edema, low blood pressure, thrombosis, cranio-cerebral and spinal trauma, premature birth, atherosclerosis, ascites in malignancy, tumor metastases, cerebral edema in tumors, heat injury to the brain, virus disorders, liver cirrhosis, and Alzheimer's disease.

The compounds of formula (I) excluded from the compounds of formula (I) under β can likewise be used for the treatment and/or prevention of liver cirrhosis and/or Alzheimer's disease.

Since it is also known that bradykinin is linked with the release of mediators, such as prostaglandins, leukotrienes, tachykinins, histamine, and thromboxanes, the compounds of formula (I) thus also have the potential for treatment and/or prevention of the diseases which are caused by these mediators.

The invention therefore also relates to the use of compounds of formula (I) as therapeutics and to pharmaceutical preparations which contain these compounds.

Pharmaceutical preparations and therapeutics contain an effective amount of the active compound of formula (I)— individually or in combination—together with an inorganic or organic pharmaceutically utilizable carrier or excipient.

Administration can be carried out enterally, parenterally—such as, for example, subcutaneously, i.m., or i.v.—, sublingually, epicutaneously, nasally, rectally, intravaginally, intrabuccally, or by inhalation. The dose of the active compound depends on various factors, such as the warm-blooded species, the body weight, the age, and the manner of administration.

The pharmaceutical preparations of the present invention are produced in a dissolving, mixing, granulating, or coating process known per se.

For administration by inhalation, atomizers or compressed gas packs using inert carrier gases can be used.

For intravenous, subcutaneous, epicutaneous, or intradermal administration, the active compounds or their physiologically tolerable salts are brought into solution, suspension, or emulsion, if desired with the pharmaceutically customary auxiliaries, for example for isotonicization or pH adjustment, and solubilizers, emulsifiers, or other auxiliaries.

Should the half-lives of the described pharmaceuticals in body fluids be inadequate, the use of injectable delayed-release preparations is useful.

Pharmaceutical forms which can be used are, for example, oily crystal suspensions, microcapsules, rods, or implants, it being possible to construct the latter from tissue-compatible polymers, in particular biodegradable polymers, for example, those based on polylactic acid-polyglycolic acid copolymers or human albumin.

A suitable dose range for forms to be administered topically and by inhalation includes solutions containing 0.01–5 mg/l; in the case of systemic administration forms, dosages in the range of 0.01–10 mg/kg are suitable.

Generally, amounts between 0.1 and 1000 mg/kg of body weight can be administered.

List of abbreviations:

| abs. | absolute |
|---|---|
| BOC | t-Butyloxycarbonyl |
| $CH_2Cl_2$ | Dichloromethane |
| DCI | Desorption Chemical Ionization |
| DMAP | Dimethylaminopyridine |
| DMF | N,N-Dimethylformamide |
| EA | Ethyl acetate |
| ESI | Electron Spray Ionization |
| FAB | Fast Atom Bombardment |
| M.p. | Melting point |
| satd | saturated |
| h | hour(s) |
| Hal | Halogen |
| MeOH | Methanol |

-continued

| min | minute(s) |
|---|---|
| RT | Room temperature |
| TOTU | O-[Cyano(ethoxycarbonyl)methylenamino]-1,1,3,3-tetramethyluronium-tetrafluoroborate |
| dec. | decomposition |

EXAMPLES

The invention is illustrated by the examples below. The experiments described in these examples, in some instances, have been performed more than one time, in order to produce sufficient amounts of product for use in later experiments. These examples should be construed as illustrating the invention and not as limiting it.

Example 1

8-[6-Chloro-2-cyano-3-(N-ethylaminocarbonylglycyl-N-methyl)amino-benzyloxy]-2-methylquinoline a) 3-Chloro-2-methyl-6-nitrobenzonitrile A solution of 10 g (49 mmol) of 2,6-dichloro-3-nitrotoluene and 4.8 g (54.0 mmol) of CuCN in 100 ml of abs. DMF was stirred at 150° C. for 6 h, a further 2.4 g (27.0 mmol) of CuCN being added after 4 h. The solvent was stripped off and the residue obtained taken up in ethyl acetate. The precipitate deposited was filtered off and extracted several times with warm ethyl acetate. The combined ethyl acetate solutions were washed with $H_2O$, dilute ammonia solution, and saturated NaCl solution, dried over $Na_2SO_4$, and concentrated to dryness. The resulting yellow, crystalline residue was purified by column chromatography on $SiO_2$ using EA/n-heptane 1:10 as a solvent. 5.8 g of the title compound resulted in the form of yellow crystals.

M.p.: 93–96° C. $R_f$ ($SiO_2$, EA/n-heptane 1:2)=0.39 MS(DCI): 197 (M+H).

b) 6-Chloro-2-cyano-3-nitrobenzyl bromide

A suspension of 5.0 g (25.4 mmol) of the compound from Example 1a) and 8.0 g (28.0 mmol) of 1,3-dibromo-5,5-dimethylhydantoin in 100 ml of chlorobenzene was stirred at 110° C. for 18 h after addition of 300 mg of benzoyl peroxide. The reaction solution was concentrated to dryness in a high vacuum, and the crystalline, brown residue was taken up in $CH_2Cl_2$. The $CH_2Cl_2$ solution was washed with $H_2O$, 5% strength $Na_2SO_3$ solution, $H_2O$, 10% strength $NaHCO_3$ solution, and finally saturated NaCl solution. Drying, concentration, and column-chromatographic purification of the residue on $SiO_2$ (EA/n-heptane 1:4) yielded 3.5 g of the title compound as beige crystals.

M.p.: 89° C. $R_f$($SiO_2$, EA/n-heptane 1:2)=0.28 MS(DCI): 275/277 (M+H).

c) 8-(6-Chloro-2-cyano-3-nitrobenzyloxy)-2-methylquinoline

A suspension of 1.4 g (9.0 mmol) of 8-hydroxyquinaldine and 2.93 g (9.0 mmol) of $Cs_2CO_3$ in 15 ml of abs. DMF was stirred at RT under an argon atmosphere for 30 min. A solution of 2.5 g (9.0 mmol) of the compound from Example 1b) in 15 ml of abs. DMF was added dropwise. The resulting yellow suspension was stirred at RT for 3 h. The reaction solution was concentrated to dryness in a high vacuum, and the residue was taken up in $CH_2Cl_2$ and washed successively with $H_2O$, 10% $NaHCO_3$, 5% $NaHSO_4$, and satd NaCl solution. Drying over $MgSO_4$, concentration, and recrystallization from EA yielded 2.4 g of the title compound in the form of yellow crystals.

M.p.: 212–215° C. $R_f$ (SiO$_2$, EA/n-heptane 1:2)=0.11 MS(DCI): 354 (M+H).

d) 8-(3-Amino-6-chloro-2-cyanobenzyloxy)-2-methylquinoline 2.0 g (5.5 mmol) of the compound from Example 1c) were dissolved in 60 ml of EA and treated with 6.2 g (27.5 mmol) of SnCl$_2$×2H$_2$O. The resulting suspension was stirred under reflux for 40 min. It was concentrated to dryness, the residue was taken up in H$_2$O, and the pH was adjusted to 9 by addition of 2N NaOH. The precipitate deposited was filtered off with suction and washed several times by stirring with warm CH$_2$Cl$_2$. Concentration of the CH$_2$Cl$_2$ solution afforded 1.4 g of the title compound in the form of a pale brown solid.

M.p.: 248–251° C. $R_f$ (SiO$_2$, EA/n-heptane)=0.13 MS(DCI): 324 (M+H).

e) 8-[6-Chloro-2-cyano-3-(N-phthaloylglycyl) aminobenzyloxy]-2-methylquinoline

A solution of 1.4 g (4.4 mmol) of the compound from Example 1d), 540.0 mg (4.4 mmol) of DMAP, 355 µl (4.4 mmol) of pyridine, and 2.2 g (6.6 mmol) of phthalimidoacetyl chloride in 100 ml of CH$_2$Cl$_2$ was stirred under reflux for 45 min. The reaction solution was washed with H$_2$O, dried over Na$_2$SO$_4$, and concentrated. The residue obtained was purified by recrystallization from methylene chloride. 1.2 g of the title compound resulted.

M.p.: 209° C. $R_f$ (SiO$_2$, CH$_2$Cl$_2$/MeOH 10:1)=0.72 MS(DCI): 511 (M+H).

f) 8-[6-Chloro-2-cyano-3-(N-phthaloylglycyl-N-methyl) aminobenzyloxy]-2-methylquinoline 1.2 g (2.3 mmol) of the compound from Example 1e) were added to a suspension of 113.0 mg (2.3 mmol) of NaH (50% strength suspension in oil) in 15 ml of abs. DMF cooled to 0° C. The mixture was stirred at 0° C. for 30 min. 163 µl (2.6 mmol) of methyl iodide were then added dropwise, and the reaction solution was stirred at 50° C. for 4 h. It was cooled, and the reaction was ended by adding of 30 ml of H$_2$O. 200 ml of CH$_2$Cl$_2$ were added, and the mixture was washed with H$_2$O, dried over Na$_2$SO$_4$, and concentrated to dryness. Column chromatography on SiO$_2$ of the residue using CH$_2$Cl$_2$/MeOH 20:1 as eluant yielded 1.0 g of the title compound as an amorphous solid.

$R_f$ (SiO$_2$, EA/n-heptane 1:1)=0.12 MS(FAB): 525 (M+H).

g) 8-[6-Chloro-2-cyano-3-(N-glycyl-N-methyl) aminobenzyloxy]-2-methylquinoline

A solution of 850.0 mg (1.6 mmol) of the compound from Example 1f) and 160 µl (3.2 mmol) of hydrazine monohydrate in 20 ml of CH$_2$Cl$_2$/methanol (3:1) was stirred under reflux for 2 h. The reaction solution was then suspended in water, the pH was adjusted to 12 by addition of 2N NaOH, and the mixture was extracted 3× using CH$_2$Cl$_2$. The combined CH$_2$Cl$_2$ extracts were dried over Na$_2$SO$_4$ and concentrated, and the residue which remained was purified by column chromatography on SiO$_2$ (CH$_2$Cl$_2$/MeOH/ NH$_4$OH 10:1:0.1). 360.0 mg of the title compound resulted as an amorphous solid.

$R_f$ (SiO$_2$, CH$_2$Cl$_2$/MeOH/NH$_4$OH 10:1:0.1)=0.23 MS(DCI): 395 (M+H).

h) 8-[6-Chloro-2-cyano-3-(N-ethylaminocarbonylglycyl-N-methyl)amino-benzyloxy]-2-methylquinoline A solution of 130.0 mg (0.3 mmol) of the compound from Example 1g) and 52 µl (0.6 mmol) of ethyl isocyanate was stirred under reflux for 45 min. It was concentrated to dryness, the residue was washed by stirring with EA, and the title compound was filtered off as a white, amorphous solid. Drying in a high vacuum afforded a yield of 66.0 mg of the title compound.

$R_f$ (SiO$_2$, CH$_2$Cl$_2$/MeOH/NH$_4$OH 10:1:0.1)=0.32 MS(DCI): 466 (M+H).

Example 2

8-[6-Chloro-2-cyano-3-[N-(4-trans-trifluoromethylcinnamoylglycyl)-N-methyl] aminobenzyloxy]-2-methylquinoline a) trans-4-Trifluoromethylcinnamoyl chloride 200.0 mg (0.92 mmol) of trans-4-trifluoromethylcinnamic acid were treated with 200 µl of thionyl chloride. After addition of 2 drops of DMF, the reaction solution obtained was stirred at 75° C. for 3 h. It was then concentrated to dryness, and the residue was taken up in toluene 2× and concentrated to dryness again. Drying in a high vacuum yielded 237.0 mg of the title compound as a slightly yellow, amorphous powder.

b) 8-[6-Chloro-2-cyano-3-[N-(4-trans-trifluoromethylcinnamoylglycyl)-N-methyl] aminobenzyloxy]-2-methylquinoline A solution of 100.0 mg (0.253 mmol) of the compound from Example 1g), 119.0 mg (0.506 mmol) of the compound from Example 2a), and 35 µl (0.253 mmol) of triethylamine in 4 ml of CH$_2$Cl$_2$ was stirred under reflux for 1 h. The reaction solution was washed with water and saturated NaCl solution, dried over Na$_2$SO$_4$, and concentrated. The resulting oily residue was purified by means of column chromatography on SiO$_2$ (CH$_2$Cl$_2$/MeOH 40:1). 102 mg of the title compound were isolated as an amorphous powder.

$R_f$ (SiO$_2$, CH$_2$Cl$_2$/MeOH 20:1)=0.32 MS(FAB): 593 (M+H)$^+$.

Example 3

8-[6-Chloro-2-cyano-3-[N-(3-methoxycinnamoylglycyl-N-methyl]amino-benzyloxy]-2-methylquinoline a) trans-3-Methoxycinnamoyl chloride The title compound was prepared by the process given in Example 2a). From 100.0 mg (0.562 mmol) of 3-methoxycinnamic acid, 120.0 mg of the title compound resulted as an amorphous solid.

b) 8-[6-Chloro-2-cyano-3-[N-(3-methoxycinnamoylglycyl-N-methyl]-aminobenzyloxy]-2-methylquinoline The title compound was prepared by reaction of the compound from Example 1g) and the compound from Example 3a) by the process given in Example 2b). From 100.0 mg (0.253 mmol) of the compound from Example 1g), 77.0 mg of the title compound were obtained as a pale yellow solid.

$R_f$ (SiO$_2$, CH$_2$Cl$_2$/MeOH 20:1)=0.20 MS(FAB): 554 (M+H)$^+$.

Example 4

8-[6-Chloro-2-cyano-3-[N-(4-methoxycarbonylbutanoylglycyl-N-methyl]-aminobenzyloxy]-2-methylquinoline 57 µl (0.456 mmol) of monomethyl glutarate, 65.0 mg (0.456 mmol) of ethyl (E)-cyanohydroximinoacetate, 155 µl (0.912 mmol) of N-ethyldiisopropylamine, and 150.0 mg (0.456 mmol) of TOTU were added to a solution of 180.0 mg (0.456 mmol) of the compound from Example 1g) in 8 ml of abs. DMF. The mixture was stirred at RT under argon for 6 h. The reaction solution was diluted with $CH_2Cl_2$ and then washed with a 10% strength $KHSO_4$ solution and a saturated $NaHCO_3$ solution. Drying over $Na_2SO_4$, concentration, and purification of the residue by column chromatography on $SiO_2$ using $CH_2Cl_2$/MeOH 40:1 as eluant yielded 156 mg of the title compound as a slightly yellow-colored, amorphous solid.

$R_f$ ($SiO_2$, $CH_2Cl_2$/MeOH 20:1)=0.28 MS(FAB): 523 $(M+H)^+$.

Example 5

8-[6-Chloro-2-cyano-3-[N-(4-carboxybutanoylglycyl-N-methyl]amino-benzyloxy]-2-methylquinoline A solution of 99.0 mg (0.189 mmol) of the compound from Example 4 in 3 ml of methanol was treated with 387 µl, (0.378 mmol) of 1N NaOH solution and stirred at RT for 14 h. The reaction solution was concentrated to dryness, the residue was taken up in a little $H_2O$, the pH of the solution was adjusted to 5 by addition of 2N HCl, and the precipitate deposited was filtered off with suction. Purification by column chromatography on $SiO_2$ ($CH_2Cl_2$/MeOH 10:1) yielded 45 mg of the title compound as a pale yellow, amorphous solid.

$R_f$ ($SiO_2$, $CH_2Cl_2$/MeOH 10:1)=0.11 MS(ESI): 509 (M+H), 523 $(M+Na+H)^+$.

Example 6

8-[6-Chloro-2-cyano-3-[N-(4-aminobutylaminocarbonylglycyl-N-methyl] aminobenzyloxy]-2-methylquinoline bistrifluoroacetate a) 8-[6-Chloro-2-cyano-3-[N-(4-tert-butyloxycarbonyl) aminobutylamino-carbonylglycyl-N-methyl] aminobenzyloxy]-2-methylquinoline 77.5 µl (0.405 mmol) of N-BOC-1,4-diaminobutane were dissolved in 2 ml of abs. DMF under an argon atmosphere, and the solution was treated with 68.9 µl (0.405 mmol) of N-ethyidiisopropylamine and 66.0 mg (0.405 mmol) of N,N-carbonyldiimidazole and stirred at RT for 3 h. 160 mg (0.405 mmol) of the compound from Example 1g) were then added, and the reaction mixture was stirred at RT for 48 h. It was diluted with EA, washed with a satd $Na_2CO_3$ solution and a 10% strength $KHSO_4$ solution, dried over $Na_2SO_4$, and concentrated. Drying in a high vacuum yielded 86 mg of the title compound as an amorphous, beige solid.

$R_f$ ($SiO_2$, $CH_2Cl_2$/MeOH 10:1)=0.33 MS(FAB): 609 $(M+H)^+$.

b) 8-[6-Chloro-2-cyano-3-[N-(4-aminobutylaminocarbonyl)glycyl-N-methyl]-aminobenzyloxy]-2-methylquinoline bistrifluoroacetate A solution of 80.0 mg (0.131 mmol) of the compound from Example 6a in 4 ml of $CH_2Cl2$ was treated with 330 µl of trifluoroacetic acid and stirred at RT for 2 h and then concentrated to dryness, and the residue was taken up in toluene 2× and again concentrated to dryness. The crystalline residue was triturated with n-heptane, filtered off with suction, and dried in a high vacuum. 78 mg of the title compound resulted as an amorphous, beige foam.

$R_f$ ($SiO_2$/MeOH/$NH_4OH$ 10:1:0.1)=0.05 MS (ESI): 509 $(M+H)^+$.

Example 7

[3-Chloro-6-[(3-ethylureido)acetyl)methylamino]-2-(2-methyiquinoline-8-yloxymethyl]benzamide A solution of 170.0 mg (0.365 mmol) of the compound from Example 1h) in 2 ml of ethanol was treated with 770 µl of a 3N $Na_2CO_3$ solution and 230 µl of a 30% strength $H_2O_2$ solution. The resulting reaction solution was stirred at RT for 17 h. It was concentrated, and the residue was taken up in $H_2O$ and extracted with $CH_2Cl_2$. The combined extracts were dried over $Na_2SO_4$ and concentrated, and the residue was purified by means of chromatography on $SiO_2$ ($CH_2Cl_2$/MeOH 15:1). 87 mg of the title compound were isolated as an amorphous, white solid.

$R_f$ ($SiO_2$, $CH_2Cl_2$/MeOH 10:1)=0.34 MS (ESI): 484 $(M+H)^+$.

Example 8

[3-Chloro-2-(2-methylquinolin-8-yloxymethyl)-6-(N-methyl-[[3-(trans-4-trifluoromethylphenyl) acryloylamino]-N-acetyl]amino)benzamide The title compound was prepared from 80.0 mg (0.134 mmol) of the compound of Example 2) by the process given in Example 7). In this case, 44.0 mg of the title compound were isolated as a white, crystalline solid.

M.p.: 124° C. (dec.) $R_f$($SiO_2$, $CH_2Cl_2$/MeOH 10:1)=0.44 MS (FAB): 611 $(M+H)^+$.

Example 9

N-[2-Cyano-4-methoxy-3-(2-methylquinolin-8-yloxymethyl)phenyl]-2-(3-ethylureido)-N-methylacetamide a) 3-Methoxy-2-methyl-6-nitrobenzonitrile 462 mg (20.14 mmol) of sodium were dissolved in 15 ml of abs. methanol at RT. This solution was added dropwise in the course of 2 h to a solution of 3.6 g (18.31 mmol) of the compound from Example 1a) in 45 ml of abs. methanol warmed to 55° C. After stirring at 55° C. for 1 h, the reaction solution was concentrated, the residue was taken up in $H_2O$/$CH_2Cl_2$, and the organic phase was separated off. The organic phase was washed with water, dried over $Na_2SO_4$, and concentrated. Purification of the resulting residue by means of column chromatography on $SiO_2$ (EA/n-heptane 1:2) yielded 2.6 g of the title compound as a white, crystalline solid.

M.p.: 128–130° C. $R_f$($SiO_2$; EA/n-heptane 2:1)=0.40 MS (DCI): 193 $(M+H)^+$.

b) 2-Cyano-6-methoxy-3-nitrobenzyl bromide

The title compound was prepared from 6.0 g (31.24 mmol) of the compound of Example 9a) by the process given in Example 1b). The yield was 7.6 g.

M.p.: 137–138° C. $R_f$($SiO_2$, EA/n-heptane 1:1)=0.29 MS (DCI): 271/273 $(M+H)^+$.

c) 8-(2-Cyano-6-methoxy-3-nitrobenzyloxy)-2-methylquinoline

The title compound was prepared from the compound of Example 9b) and 8-hydroxyquinaldine by the process given in Example 1c). In this case, from 6.6 g (24.3 mmol) of the compound from Example 9b), 7.35 g of the title compound resulted as a white, crystalline solid.

M.p.: 227–230° C. $R_f$(SiO$_2$, EA/n-heptane 2:1)=0.10 MS (DCI): 350 (M+H)$^+$.

d) 8-(3-Amino-2-cyano-6-methoxybenzyloxy)-2-methylquinoline

The title compound was prepared from the compound from Example 9c) by the process given in Example 1d). From 6.15 g (17.58 mmol) of the compound from Example 9c), 3.6 g of the title compound were obtained.

M.p.: 188–191° C. $R_f$(SiO$_2$, EA/n-heptane 4:1)=0.20 MS (DCI)=320 (M+H)$^+$.

e) 8-[2-Cyano-6-methoxy-3-(N-phthaloylglycyl)aminobenzyloxy]-2-methylquinoline

The title compound resulted from the reaction of the compound from Example 9d) with phthalimidoacetyl chloride by the process given in Example 1e). From 2.6 g (8.14 mmol) of the compound from Example 9d), 3.06 g of the title compound were obtained.

M.p.: 102–105° C. $R_f$ (SiO$_2$, CH$_2$Cl$_2$ 4:19=0.34 MS (ESI): 507 (M+H)$^+$.

f) 8-[2-Cyano-6-methoxy-3-(N-phthaloylglycyl-N-methyl)amino-benzyloxy]-2-methylquinoline The title compound was prepared from the compound from Example 9e) by the process given in Example 1f). From 2.4 g (9.60 mmol) of the compound from Example 9e), 2.2 g of the desired compound resulted as an amorphous powder.

$R_f$ (SiO$_2$, CH$_2$Cl$_2$/EA 4:1)=0.10 MS (ESI): 521 (M+H)$^+$.

g) 8-[2-Cyano-6-methoxy-3-(N-glycyl-N-methyl)aminobenzyloxy]-2-methylquinoline

The title compound was prepared from the compound of Example 9f) analogously to the process given in Example 1g). From 630.0 mg (1.21 mmol) of the compound from Example 9f), 368.0 mg of the title compound were obtained.

M.p.: 218–220° C. $R_f$ (SiO$_2$, EA/n-heptane)=0.12 MS (DCI): 391.

h) 8-[2-Cyano-6-methoxy-3-(N-ethylaminocarbonylglycyl-N-methyl)-aminobenzyloxy]-2-methylquinoline 80.0 mg (0.20 mmol) of the compound from Example 9g) were reacted with ethyl isocyanate by the process given in Example 1h). 70.0 mg of the title compound were isolated.

M.p.: 109–111° C. $R_f$ (SiO$_2$, CH$_2$Cl$_2$/MeOH 18:2)=0.15 MS (FAB): 462 (M+H)$^+$.

Example 10

8-[3-(N-(4-trans-Trifluoromethylcinnamoylglycyl)-N-methylamino)-20 2,6-dimethylbenzyloxy]-2-methylquinoline a) 2,6-Dimethyl-3-nitrobenzoic acid 13.5 g (90.0 mmol) of 2,6-dimethylbenzoic acid were introduced in portions into a solution of 25 ml of conc. sulfuric acid and 25 ml of 65% strength HNO$_3$ cooled to 0° C. After stirring at 0° C. for 1 h, the reaction mixture was poured onto ice, and the precipitate deposited was filtered off with suction and dried. 15.5 g of the title compound resulted.

M.p.: 109° C. MS (DCI): 196 (M+H)$^+$.

b) 2,6-Dimethyl-3-nitrobenzyl alcohol 4.2 g (20.4 mmol) of benzyltriethylammonium borohydride in 30 ml of CH$_2$Cl$_2$ were treated at 0° C. with 2.6 ml (20.4 mmol) of trimethylchlorosilane. After stirring at 0° C. for 15 min, a solution of 2.0 g (10.2 mmol) of the compound from Example 10a) in 10 ml of CH$_2$Cl$_2$ was added dropwise to this reaction solution. After stirring for 2 h, the reaction solution was poured onto a 5% strength NaHCO$_3$ solution and then extracted 3× with EA. The combined organic phases were washed with 5% strength NaHCO$_3$ solution, water, and saturated NaCl solution, dried over MgSO$_4$, and concentrated. High-vacuum drying afforded 700.0 mg of the title compound.

$R_f$ (SiO$_2$, EA)=0.31 MS (DCI): 182 (M+H)$^+$.

c) 2,6-Dimethyl-3-nitrobenzyl trifluoromethanesulfonate

A solution of 340.0 mg (1.80 mmol) of the compound from Example 10b) was treated under an argon atmosphere with 200.0 mg (1.80 mmol) of triethylamine and 230.0 mg (18 mmol) of methanesulfonyl chloride. After stirring for 30 min, the reaction mixture was poured onto water and extracted several times with CH$_2$Cl$_2$. The combined CH$_2$Cl$_2$ extracts were dried over MgSO$_4$ and concentrated, and the residue was dried in a high vacuum. 450.0 mg of the title compound were isolated.

MS (DCI):260 (M+H)$^+$.

d) 8-(2,6-Dimethyl-3-nitrobenzyloxy)-2-methylquinoline

A solution of 270.0 mg (1.70 mmol) of 8-hydroxy-2-methylquinoline, 450.0 mg (1.70 mmol) of the compound from Example 10c), and 570.0 mg (1.70 mmol) of Cs$_2$CO$_3$ in 2 ml of abs. DMF were stirred at RT overnight. The reaction solution was treated with methyl tert-butyl ether, washed 2× with 2N NaOH, and dried over MgSO$_4$. Concentration and high-vacuum drying yielded 510.0 mg of the title compound.

$R_f$ (SiO$_2$, EA/n-heptane 1:1)=0.48 MS (DCI): 323 (M+H)$^+$.

e) 8-(3-Amino-2,6-dimethylbenzyloxy)-2-methylquinoline

The title compound was prepared from the compound of Example 10d) by the process given in Example 1d). From 500.0 mg (1.5 mmol) of the compound from Example 10d), 450.0 mg of the title compound were obtained.

$R_f$(SiO$_2$, EA/heptane 1:1)=0.21 MS (DCI): 293 (M+H)$^+$.

f) 8-[2,6-Dimethyl-3-(N-phthaloylglycyi)aminobenzyloxy]-2-methylquinoline

The title compound was prepared from the compound from Example 10e) by the process given in Example 1e). From 440.0 mg (1.4 mmol) of the compound from Example 10e), 630 mg of the title compound resulted.

$R_f$ (SiO$_2$, EA)=0.42 MS (DCI): 480 (M+H)$^+$.

g) 8-[2,6-Dimethyl-3-(N-phthaloylglycyl-N-methyl)aminobenzyloxy]-2-methylquinoline The title compound was prepared from the compound of Example 10f) by the process given in Example 1f). From 610.0 mg (1.27 mmol) of the compound from Example 10f), 480.0 mg of the title compound resulted as a slightly yellow-colored oil.

$R_f$ (SiO$_2$, EA/n- heptane 1:1)=0.19 MS (DCI)=494 (M+H)$^+$.

h) 8-[2,6-Dimethyl-3-(N-glycyl-N-methyl)aminobenzyloxy]-2-methylquinoline

The title compound was prepared from the compound of Example 10g) by the process given in Example 1g). From 470.0 mg (0.96 mmol) of the compound from Example 10g), 180.0 mg of the title compound resulted as a slightly yellow-colored oil.

$R_f$ (SiO$_2$, EA/n-heptane)=0.14 MS (DCI): 364 (M+H)$^+$.

i) 8-[3-(N-(trans-4-Trifluoromethylcinnamoylglycyl)-N-methylamino)-2,6-dimethylbenzyloxy]-2-methylquinoline A solution of 175.0 mg (0.48 mmol) of the compound from Example 10h), 107 mg (0.49 mmol) of 4-trans-trifluoromethylcinnamic acid, 102.0 mg (0.49 mmol) of N,N'-dicyclohexylcarbodiimide ("DCC"), and 100.0 mg (0.49 mmol) of N-hydroxybenzotriazole in 4 ml of abs. DMF was stirred at RT overnight under an argon atmosphere. The resulting reaction mixture was diluted with EA, washed with a satd $Na_2CO_3$ solution and a 10% strength $NaHSO_4$ solution, and dried over $MgSO_4$. The solvent was removed in vacuo, and the residue was purified by column chromatography on $SiO_2$ (EA). 50 mg of the title compound were isolated as an amorphous solid.

$R_f$ ($SiO_2$, EA)=0.40 MS (FAB): 562 $(M+H)^+$.

Example 11

8-[6-Chloro-2-methoxy-3-(N-(4-trans-trifluoromethylcinnamoylglycyl)-N-methylamino)benzyloxy]-2-methylquinoline a) 2-Chloro-6-methoxy- and 6-chloro-2-methoxy-3-nitrotoluene 5.8 ml (0.145 mol) of methanol were added at 0° C. to a suspension of 5.8 g (0.145 mol) of sodium hydride (60% strength suspension in mineral oil) in 200 ml of DMF. After stirring at this temperature for 30 min, 30 g (0.145 mol) of 2,6-dichloro-3-nitrobenzene were added in portions, the temperature rising to ~20° C. The mixture was then stirred without cooling for 1.5 h and, after addition of ~300 g of ice, extracted 3× with ethyl acetate (3×800 ml). The extracts were dried over $MgSO_4$ and concentrated in vacuo. Column chromatography on $SiO_2$ using EA/n-heptane as an eluant yielded the two title compounds as oils.

α) 2-Methoxy-6-chloro-3-nitrobenzene
Yield: 8.0 g
$R_f$ ($SiO_2$, EA/n-heptane 1:2)=0.4
MS (DCI): 202 (M+H).

β) 2-Chloro-6-methoxy-3-nitrobenzene
Yield: 2.6 g
$R_f$ ($SiO_2$, EA/n-heptane 1:2)=0.25
MS (DCI): 202 (M+H).

b) 2-Methoxy-6-chloro-3-nitrobenzyl bromide

A mixture of 5.8 g (20.0 mmol) of 1,3-dibromo-5,5-dimethylhydantoin and 0.5 g of azobisisobutyronitrile was added in portions at 110° C. to a solution of 8.0 g (40.0 mmol) of 2-methoxy-6-chloro-3-nitrotoluene from Example 11aα) in 50 ml of chlorobenzene. After 1 h, a mixture of 3.0 g (10 mmol) of 1,3-dibromo-5,5-dimethylhydantoin and 0.2 g of azobisisobutyronitrile was again added. After a further 1.5 h, the mixture was allowed to cool, and 500 ml of ethyl acetate were added to the reaction solution. The resulting mixture was washed once each with satd $Na_2SO_3$ solution, $Na_2CO_3$ solution, and NaCl solution, dried ($MgSO_4$), and concentrated. 10.2 g of the title compound resulted in the form of an amorphous powder.

$R_f$ ($SiO_2$, EA/n-heptane 1:4)=0.45 MS (DCI): m/e =280 (M+H).

c) 8-(2-Methoxy-3-nitro-6-chlorobenzyloxy)-2-methylquinoline 10.8 g (33.9 mmol) of $Cs_2CO_3$ were added at RT to a solution of 5.0 g (33.9 mmol) of 8-hydroxy-2-methylquinoline in 65 ml of DMF. After stirring for 30 min, 9.5 g (34.0 mmol) of the compound from Example 11b) were added to the reaction solution. After stirring at RT for 18 h, the mixture was treated with water, and the precipitate obtained was filtered off with suction and washed with 50 ml of EA. Drying in a high vacuum afforded 10.4 g of the title compound as an amorphous powder.

$R_f$ ($SiO_2$, EA/n-heptane 1:1)=0.40 MS (FAB): m/e =359 (M+H).

d) 8-(2-Methoxy-3-amino-6-chlorobenzyloxy)-2-methylquinoline 4.9 g (13.7 mmol) of the compound from Example 11c) in 60 ml of EA were treated with 15.0 g (66.6 mmol) of $SnCl_2$×2 $H_2O$, and the suspension obtained was stirred at 70° C. for 1 h. After cooling to RT, it was concentrated in vacuo, and the residue obtained was then treated with 100 ml of 20% strength NaOH solution. Extraction several times with $CH_2Cl_2$, drying of the combined organic phases over $CaCl_2$, and concentration thereof yielded 4.2 g of the title compound.

$R_f$ (EA/n-heptane 1:1)=0.15 MS (DCI): m/e=329 (M+H).

e) 8-(2-Methoxy-3-phthaloylglycylamino-6-chlorobenzyloxy)-2-methylquinoline 3.3 g (10 mmol) of the compound from Example 11d) and 1.2 g (10 mmol) of DMAP in 30 ml of N-methylpyrrolidone and 10 ml of pyridine were treated with 3.4 g (15.0 mmol) of phthaloylglycyl chloride. The mixture was heated to 50° C. for 1.5 h, then cooled to 0° C., and 30 ml of $H_2O$ were subsequently added. The precipitate deposited was filtered off with suction and washed with 100 ml of EA. 4.3 g of the title compound resulted as an amorphous powder.

$R_f$ ($SiO_2$, EA/n—heptane 1:1)=0.10 MS (FAB): m/e=516 (M+H).

f) 8-[2-Methoxy-3-(N-methyl-N-phthaloylglycyl)amino-6-chlorobenzyloxy]-2-methylquinoline 313.0 mg (8 mmol) of sodium hydride (60% strength suspension) were added at 0° C. to a solution of 3.7 g (7.1 mmol) of the compound from Example 11e) in 40 ml of DMF. After 30 min, 0.5 ml (8.0 mmol) of methyl iodide was injected. The mixture was subsequently stirred at RT for 1 h, then cooled to 0° C., and 75 ml of $H_2O$ were added. The precipitate deposited was filtered off with suction and washed with 30 ml of cold methanol. 3.3 g of the title compound were isolated.

$R_f$ ($SiO_2$, EA/n-heptane 1:1)=0.12 MS (FAB)=m/e=530 $(M+H)^+$.

g) 8-[2-Methoxy-3-(N-methyl-N-glycyl)amino-6-chlorobenzyloxy]-2-methylquinoline

A solution of 1.4 g (2.8 mmol) of the compound from Example 11f) and 0.54 ml (11.2 mmol) of hydrazine hydrate in 60 ml of ethanol was stirred at RT for 12 h. It was concentrated, 40 ml of $CH_2Cl_2$ were added, the mixture was filtered, and the solid residue was extracted with 40 ml of $CH_2Cl_2$. Concentration of the $CH_2Cl_2$ solution yielded 0.9 g of the title compound as a pale yellow foam.

$R_f$ ($SiO_2$, EA/$CH_3OH$ 1:1)=0.20 MS (FAB): m/e =400 (M+H).

h) 8-[6-Chloro-2-methoxy-3-(N-4-trans-trifluoromethylcinnamoylglycyl)-N-methylamino)benzyloxy]-2-methylquinoline The title compound was prepared by reaction of the compound from Example 11g) with the compound from Example 2a) by the process given in Example 2b). From 250.0 mg of the compound from Example 11g), 140.0 mg (0.62 mmol) of the desired compound resulted as an amorphous solid.

$R_f$ ($SiO_2$, EA)=0.40 MS (DCI): 598 $(M+H)^+$.

Example 12

8-[6-Chloro-2-methoxy-3-(N-(3-(2-furyl)acrylglycyl)-N-methyl)amino-benzyloxy]-2-methylquinoline The title compound resulted from the reaction of the compound from Example 11g) with β-furylacrylic acid by the process given in Example 4). From 200 mg (0.5 mmol) of the compound from Example 11g), 39 mg of the title compound were prepared.

$R_f$ (SiO$_2$, EA)=0.20 MS (FAB): 520 (M+H)$^+$.

Example 13

8-[6-Chloro-2-hydroxy-3-(N-(trans-4-methylcinnamoylglycyl-N-methyl)-aminobenzyloxy]-2-methylquinoline a) 8-[6-Chloro-2-methoxy-3-(N-(trans-4-methylcinnamoylglycyl-N-methyl)-aminobenzyloxy]-2-methylquinoline The title compound was prepared by reaction of the compound from Example 11g) with Z-4-methylcinnamic acid by the process given in Example 10i). From 330 mg (0.83 mmol) of the compound from Example 11g), 200 mg of the title compound were obtained.

$R_f$ (SiO$_2$, EA): 0.22 MS (FAB): 544 (M+H)$^+$.

b) 8-[6-Chloro-2-hydroxy-3-(N-(trans-4-methylcinnamoylglycyl-N-methyl)-aminobenzyloxy]-2-methylquinoline A solution of 200 mg (0.37 mmol) of the compound from Example 13a) and 1.5 ml of a 1M boron tribromide solution (in CH$_2$Cl$_2$) in 10 ml of abs. CH$_2$Cl$_2$ was stirred at RT for 72 h under argon. The reaction solution was subsequently treated with 20 ml of ethanol and then concentrated to dryness. The residue obtained was treated with H$_2$O, and the aqueous solution was extracted several times with EA. The combined EA extracts were washed with satd NaCl soln, dried over MgSO$_4$, and concentrated. Purification of the residue by chromatography on SiO$_2$ (EA) yielded 50 mg of the title compound as an amorphous substance.

$R_f$ (SiO$_2$, EA)=0.37 MS (FAB): 530 (M+H)$^+$.

Example 14

8-[2-Chloro-6-methoxy-3-(N-(4-trans-trifluoromethylcinnamoylglycyl-N-methyl)amino) benzyloxy]-2-methylquinoline a) 2-Chloro-6-methoxy-3-nitrobenzyl bromide The title compound was prepared from the compound from Example 11aβ) by the process given in Example 11b). From 2.2 g (10.9 mmol) of the compound from Example 11aβ), 2.8 g of the title compound resulted as an amorphous substance.

$R_f$ (SiO$_2$, EA/heptane 1:4)=0.26 MS (DCI): 280 (M+H)$^+$.

b) 8-(2-Chloro-6-methoxy-3-nitrobenzyloxy)-2-methylquinoline

The title compound was prepared from the compound from Example 14a) by the process given in Example 11c). From 2.7 g (9.6 mmol) of the compound from Example 14a), 2.1 g of the title compound resulted as a beige, amorphous substance.

$R_f$ (SiO$_2$, EA/heptane 1:1)=0.38 MS (DCI)=359 (M+H)$^+$.

c) 8-(2-Chloro-6-methoxy-3-aminobenzyloxy)-2-methylquinoline

The title compound was prepared from the compound of Example 14b) by the process given in Example 11d). From 1.6 g (4.5 mmol) of the compound from Example 14b), 0.90 g of the title compound resulted as an amorphous, yellow solid.

$R_f$ (SiO$_2$, EA/n-heptane 1:1)=0.13 MS (DCI): 329 (M+H)$^+$.

d) 8-[2-Chloro-6-methoxy-3-(N-phthaloylglycyl) aminobenzyloxy]-2-methylquinoline The title compound was prepared from the compound of Example 14c) by the process given in Example 11e). From 0.88 g (2.68 mmol) of the compound from Example 14c), 0.81 g of the title compound was obtained.

$R_f$ (SiO$_2$, EA/n-heptane)=0.10 MS (DCI): 516 (M+H).

e) 8-[2-Chloro-6-methoxy-3-(N-phthaloylglycyl-N-methyl)aminobenzyloxy]-2-methylquinoline The title compound was prepared from the compound of Example 14d) by the process given in Example 11f). From 0.8 g (1.6 mmol) of the compound from Example 14d), 0.46 g of the title compound resulted.

$R_f$ (SiO$_2$, EA/n-heptane 2:1)=0.17 MS (DCI): 530 (M+H)$^+$.

f) 8-[2-Chloro-6-methoxy-3-(N-glycyl-N-methyl) aminobenzyloxy]-2-methylquinoline The title compound was prepared from the compound of Example 14e) by the process given in Example 11g). From 0.45 g (0.85 mmol) of the compound from Example 14e), 220 mg of the title compound were isolated in the form of a yellow oil.

$R_f$ (SiO$_2$, EA/MeOH 1:1)=0.05 MS (DCI): 400 (M+H)$^+$.

g) 8-[2-Chloro-6-methoxy-3-(N-(4-trans-trifluoromethylcinnamoylglycyl-N-methyl)amino) benzyloxy]-2-methylquinoline The title compound was prepared from the compound of Example 14f) by the process given in Example 2b). From 200 mg (0.50 mmol) of the compound from Example 14f), 60.0 mg of the title compound resulted as an amorphous solid.

$R_f$ (SiO$_2$, EA)=0.31 MS (FAB)=598 (M+H)$^+$.

Example 15

8-[2-Chloro-6-methoxy-3-(N-(3-(2-furyl) acrylglycyl)-N-methyl)amino-benzyloxy]-2-methylquinoline The title compound resulted from the reaction of the compound from Example 14f) with β-furylacrylic acid by the process given in Example 10i). From 150 mg (0.38 mmol) of the compound from Example 14f), 35 mg of the title compound were obtained as an amorphous solid.

$R_f$ (SiO$_2$, EA)=0.19 MS (ESI): 520 (M+H)$^+$.

Example 16

8-[2-Methoxy-6-thiomethyl-3-(N-(4-trans-trifluoromethylcinnamoylglycyl-N-methyl) aminobenzyloxy]-2-methylquinoline a) 8-(2-Methoxy-3-nitro-6-methylthiobenzyloxy)-2-methylquinoline A solution of 1.6 g (4.50 mmol) of the compound from Example 11c) in 40 ml of abs. DMF was treated with 320 mg (4.5 mmol) of sodium thiomethylate under an argon atmosphere. The reaction solution was stirred at RT for 24 h and then treated with 20 ml of H$_2$O. The precipitate deposited was filtered off with suction, washed with 100 ml of H$_2$O, and dried in vacuo at 50° C. for 3 h. 1.5 g of the title compound resulted.

$R_f$ (SiO$_2$, EA/heptane 1:1)=0.37 MS (DCI): 371 (M+H)$^+$.

b) 8-(3-Amino-2-methoxy-6-methylthiobenzyloxy)-2-methylquinoline

The title compound was prepared from the compound from Example 16a) by the process given in Example 11d). From 1.45 g (4.10 mmol) of the compound from Example 16a), 1.27 g of the title compound resulted.

$R_f$ (SiO$_2$, EA/heptane 1:1)=0.29 MS (FAB): 341 (M+H)$^+$.

c) 8-[2-Methoxy-6-methylthio-3-N-phthaloylglycyl) aminobenzyloxy]-2-methylquinoline The title compound was prepared from the compound from Example 16b) by the process given in Example 11e). From 1.20 g (3.53 mmol) of the compound from Example 16b), 1.35 g of the desired compound resulted.

$R_f$ (SiO$_2$, EA/heptane 2:1)=0.65 MS (FAB): 528 (M+H)$^+$.

d) 8-[2-Methoxy-6-methylthio-3-(N-phthaloylglycyl-N-methyl)amino-benzyloxy]-2-methylquinoline The title compound was prepared from the compound from Example 16c) by the process given in Example 11f). From 1.3 g (2.5 mmol) of the compound from Example 16c), 0.80 g of the desired compound resulted as an amorphous, slightly yellow-colored solid.

$R_f$ (SiO$_2$, EA/n-heptane 2:1)=0.25 MS (FAB): 542 (M+H)$^+$.

e) 8-[2-Methoxy-6-methylthio-3-(N-glycyl-N-methyl) aminobenzyloxyl-2-methylquinoline The title compound was prepared from the compound of Example 16d) by the process given in Example 11g). From 760 mg (1.50 mmol) of the compound from Example 16d), 390 mg of the title compound were obtained as an amorphous foam.

$R_f$ (SiO$_2$, EA/n-heptane 2:1)=0.04 MS (FAB): 412 (M+H)$^+$.

f) 8-[2-Methoxy-6-thiomethyl-3-(N-(4-trans-trifluoromethylcinnamoylglycyl-N-methyl) aminobenzyloxy]-2-methylquinoline The title compound resulted from reaction of the compound from Example 16e) with the compound from Example 2a) by the process given in Example 2b). From 150 mg of the compound of Example 16e), 42 mg of the title compound were isolated as an amorphous substance.

$R_f$ (SiO$_2$, EA)=0.37 MS (FAB)=610 (M+H)$^+$.

Example 17

8-[2-Methoxy-6-methylthio-3-N-5-methoxycarbonylpentanoylglycyl-N-methyl) aminobenzyloxy]-2-methylquinoline The title compound was prepared by reaction of the compound from Example 16e) with monomethyl adipate by the process given in Example 4). From 200 mg (0.49 mmol) of the compound from Example 16e), 69 mg of the title compound resulted.

$R_f$ (SiO$_2$, EA)=0.14 MS (FAB): 554 (M+H)$^+$.

Example 18

8-[6-Methoxy-2-methylthio-3-(3-(6-acetylaminopyridin-3-yl)acryloyglycyl-N-methyl) aminobenzyloxy]-2-methylquinoline a) 8-(6-Methoxy-2-methylthio-3-nitrobenzyloxy)-2-methylquinoline The title compound was prepared by reaction of the compound from Example 14b) with sodium thiomethylate analogously to the process described in Example 16a). From 4.0 g (11.16 mmol) of the compound from Example 14b), 3.0 g of the title compound were obtained as an amorphous, beige powder.

$R_f$ (SiO$_2$, EA/n-heptane 1:1) 0.19 MS (ESI): 371 (M+H)$^+$.

b) 8-(3-Amino-6-methoxy-2-methylthiobenzyloxy)-2-methylquinoline

The title compound was prepared from the compound of Example 18a) by the process described in Example 11d). From 2.7 g (7.30 mmol) of the compound from Example 18a), 2.3 g of the desired compound were obtained.

$R_f$ (SiO$_2$, EA/n-heptane 2:1)=0.18 MS (DCI): 341 (M+)$^+$.

c) 8-(6-Methoxy-2-methylthio-3-(N-phthaloylglycyl) aminobenzyloxy)-2-methylquinoline The title compound was prepared from the compound of Example 18b) by the process described in Example 11e). From 2.20 g (6.47 mmol) of the compound from Example 18b), 3.32 g of the title compound were synthesized.

$R_f$ (SiO$_2$, EA/n-heptane 2:1)=0.27 MS (ESI): 528 (M+H)$^+$.

d) 8-(6-Methoxy-2-methylthio-3-(N-phthaloylglycyl-N-methyl)aminobenzyl-oxy]-2-methylquinoline The title compound was prepared from the compound of Example 18c) by the process described in Example 11f). From 3.30 g (6.24 mmol) of the compound from Example 18c), 1.68 g of the title compound resulted as a beige solid.

$R_f$ (SiO$_2$, EA/heptane 2:1)=0.20 MS (ESI): 542 (M+H)$^+$.

e) 8-[6-Methoxy-2-methylthio-3-(N-glycyl-N-methyl) aminobenzyloxy]-2-methylquinoline The title compound was prepared from the compound from Example 18d) by the process given in Example 11g). From 1.65 g (3.0 mmol) of the compound from Example 18d), 810 mg of the title compound resulted as a beige, solid foam.

$R_f$ (SiO$_2$, EA/n-heptane 3:1)=0.06 MS (DCI): 412 (M+H)$^+$.

f) 8-[6-Methoxy-2-methylthio-3-(3-(6-acetylaminopyridin-3-yl)acryloylglycyl-N-methyl) aminobenzyloxy]-2-methylquinoline The title compound resulted from the reaction of the compound from Example 18e) with the acid chloride derivative of (E)-3-(6-acetylamino-3-pyridyl)acrylic acid (disclosed in EP-A-622 361, preparation 50) by the process described in Example 2b). From 250 mg (0.61 mmol) of the compound of Example 18e), 128 mg of the title compound were obtained.

$R_f$(SiO$_2$, EA/MeOH 10:1)=0.31 MS (FAB): 600 (M+H)$^+$.

Example 19

8-[6-Methoxy-2-methylthio-3-(N-trans-4-trifluoromethyicinnamoylglycyl-N-methyl) aminobenzyloxy]-2-methylquinoline The title compound was synthesized from the compound from Example 18e) and the compound from Example 2a) by the process described in Example 2b). From 250 mg (0.61 mmol) of the compound 18e), 70 mg of the title compound resulted as an amorphous substance.

$R_f$ (SiO$_2$, EA)=0.25 MS (FAB): 610 (M+H)$^+$.

Example 20

8-[6-Methoxy-2-methylthio-3-(N-5-methoxycarbonylpentanoylglycyl-N-methyl) aminobenzyloxy]-2-methylquinoline The title compound was prepared by reaction of the compound from Example 18e) with monomethyl adipate by the process given in Example 10i). From 300 mg (0.73 mmol) of the compound from Example 18e), 122 mg of the title compound resulted as an amorphous substance.

$R_f$(SiO$_2$, EA/MeOH 1:10)=0.28 MS (FAB): 554 (M+H)$^+$.

Example 21

8-[2,6-Dimethoxy-3-(N-(trans-4-trifluoromethylcinnamoylglycyl-N-methyl)-aminobenzyloxy]-2-methylquinoline a) 2,6-Dimethoxy-3-nitrotoluene 11.62 g (76.45 mmol) of 2,6-dimethoxytoluene were introduced in portions into 40 ml of concentrated nitric acid cooled to 0° C. After stirring at 0° C. for 15 min, the reaction solution was poured onto 250 ml of ice and extracted 3× with EA. The combined EA extracts were dried over $Na_2SO_4$, the solvent was removed in vacuo, and the brown oily residue was purified by means of column chromatography on $SiO_2$ (EA/heptane 1:8). 8.59 g of the title compound were isolated in the form of a red oil.

$R_f$ ($SiO_2$, EA/heptane 1:8)=0.28 MS (DCI): 198 (M+H)$^+$.

b) 2,6-Dimethoxy-3-nitrobenzyl bromide

The title compound was prepared from the compound of Example 21a) by the process described in Example 1b). From 8.56 g (43.60 mmol) of the compound from Example 21a), 9.19 g of the title compound were synthesized as a yellow solid.

M.p.: 69–73° C. $R_f$ ($SiO_2$, EA/n-heptane 1:4)=0.30 MS (DCI): 276/278 (M+H)$^+$.

c) 8-(2,6-Dimethoxy-3-nitrobenzyloxy)-2-methylquinoline

The title compound was prepared by reaction of the compound from Example 21b) and 8-hydroxy-2-methylquinoline by the process described in Example 1c). From 4.0 g (14.49 mmol) of the compound from Example 21b), 4.33 g of the title compound were obtained as a beige solid.

M.p.: 193–195° C. $R_f$($SiO_2$, EA/n-heptane 1:2)=0.11 MS (DCI): 355 (M+H)$^+$.

d) 8-(3-Amino-2,6-dimethoxybenzyloxy)-2-methylquinoline

The title compound was prepared from the compound from Example 21c) by the process described in Example 1d). From 4.30 g (12.20 mmol) of the compound from Example 21c), 2.28 g of the title compound resulted in the form of orange-colored crystals.

M.p.: 155–159° C. $R_f$($SiO_2$, EA/n-heptane 2:1)=0.19 MS (ESI): 325 (M+H)$^+$.

e) 8-[2,6-Dimethoxy-3-(N-phthaloylglycyi) aminobenzyioxy]-2-methylquinoline

The title compound was prepared from the compound of Example 21d) by the process given in Example 1e). From 2.27 g (7.00 mmol) of the compound of Example 21d), 2.46 g of the title compound resulted as a yellow solid.

M.p.: 196–199° C. $R_f$ ($SiO_2$, $CH_2Cl_2$/MeOH 10:1)=0.72 MS (ESI): 512 (M+H)$^+$.

f) 8-[2,6-Dimethoxy-3-(N-phthaloylglycyl-N-methyl) aminobenzyloxy]-2-methylquinoline The title compound was prepared from the compound from Example 21e) by the process described in Example 1f). From 2.45 g (4.81 mmol) of the compound from Example 21e), 1.2 g of the title compound resulted in the form of a yellow-colored, amorphous solid.

$R_f$ ($SiO_2$, EA/heptane 2:1)=0.21 MS (ESI): 526 (M+H)$^+$.

g) 8-[2,6-Dimethoxy-3-(N-glycyl-N-methyl) aminobenzyloxy]-2-methylquinoline

The title compound was prepared from the compound of Example 21f) by the process given in Example 1g). From 1.18 g (2.28 mmol) of the compound from Example 21f), 549 mg of the title compound resulted as a solid yellow foam.

$R_f$ ($SiO_2$, $CH_2Cl_2$/MeOH/$NH_4$OH 10:1:0.1)=0.34 MS (FAB): 396 (M+H)$^+$.

h) 8-[2,6-Dimethoxy-3-(N-trans-4-trifluoromethylcinnamoylglycyl-N-methyl) aminobenzyloxy]-2-methylquinoline The title compound was prepared by reaction of the compound from Example 21g) with the compound from Example 2a). From 90 mg (0.23 mmol) of the compound from Example 21g), 74 mg of the title compound resulted as a yellow-colored amorphous solid.

$R_f$ ($SiO_2$, $CH_2Cl_2$/MeOH/$NH_4$ OH 10:1:0.1)=0.67 MS (FAB): 594 (M+H)$^+$.

Example 22

8-[6-Methoxy-2-propyloxy-3-(N-(trans-4-trifluoromethylcinnamoylglycyl-N-methyl) aminobenzyloxy]-2-methylquinoline a) 6-Methoxy-2-propyloxy-3-nitrotoluene 2.0 g (10.93 mmol) of 3-methoxy-2-methyl-6-nitrophenol (prepared according to R. A. Raphael, P. Ravenscoft, *J. Chem. Soc. Perkin Trans. I*, (1988), 1823–1828) were added in portions under an argon atmosphere to a suspension of 525 mg (1 2.02 mmol) of NaH in 30 ml of abs. DMF cooled to 0° C. After stirring at 0° C. for 30 min, 1.17 ml (12.70 mmol) of n-propyl bromide were added dropwise. The reaction solution was stirred at 70° C. for 8 h. Subsequently, 70 ml of $H_2O$ were added with ice cooling, and the mixture was then concentrated to dryness. The residue was taken up in EA, and the solution was washed 3× with $H_2O$, dried over $Na_2SO_4$, and concentrated. Drying in a high vacuum afforded 2.37 g of the title compound in the form of a brown oil.

$R_f$ ($SiO_2$, EA/n-heptane 1:3)=0.45 MS (DCI): 226 (M+H)$^+$.

b) 6-Methoxy-2-propyloxy-3-nitrobenzyl bromide

The title compound was prepared from the compound of Example 22a) by the process given in Example 1b). From 3.27 g (14.53 mmol) of the compound from Example 22a), 2.77 g of the title compound resulted as a brown solid.

M.p.: 53–55° C. $R_f$ ($SiO_2$, EA/n-heptane 1:3)=0.40 MS (DCI): 304/306 (M+H)$^+$.

c) 8-(6-Methoxy-2-propyloxy-3-nitrobenzyloxy)-2-methylquinoline

The title compound was prepared by reaction of the compound from Example 22b) and 8-hydroxy-2-methylquinoline by the process given in Example 1c). From 2.77 g (9.11 mmol) of the compound from Example 22b), 2.73 g of the title compound resulted in the form of a beige solid.

M.p.: 159–161° C. $R_f$($SiO_2$, EA/n-heptane 1:2)=0.19 MS (ESI): 383 (M+H)$^+$.

d) 8-(3-Amino-6-methoxy-2-propyloxybenzyloxy)-2-methylquinoline

The title compound was prepared from the compound of Example 22c) by the process given in Example 1d). From 2.73 g (7.15 mmol) of the compound from Example 22c), 1.47 g of the title compound resulted as a pale brown solid.

M.p.: 163–165° C. $R_f$($SiO_2$, EA/n-heptane 2:1)=0.30 MS (ESI): 353 (M+H)$^+$.

e) 8-[6-Methoxy-2-propyloxy-3-(N-phthaloylglycyl) aminobenzyloxy]-2-methylquinoline The title compound was prepared from the compound of Example 22d), by the process given in Example 1e). From 1.42 g (4.03 mmol) of the compound from Example 22d), 1.76 g of the title compound resulted as a beige solid.

M.p.: 200–203° C. $R_f$($SiO_2$, $CH_2Cl_2$/MeOH 20:1)=0.30 MS (ESI): 540 (M+H)$^+$.

f) 8-[6-Methoxy-2-propyloxy-3-(N-phthaloylglycyl-N-methyl)amino-benzyloxy]-2-methylquinoline The title compound was prepared from the compound of Example 22e) by the process given in Example 1f). From 1.76 g (3.26 mmol) of the compound from Example 22e), 1.09 g of the title compound resulted as a solid, pale yellow foam.

M.p.: 63° C. (softening) $R_f$ (SiO$_2$, EA/n-heptane 3:1)= 0.35 MS (ESI): 554 (M+H)$^+$.

g) 8-[6-Methoxy-2-propyloxy-3-(N-glycyl-N-methyl) aminobenzyloxy]-2-methylquinoline The title compound was prepared from the compound of Example 22f) by the process given in Example 1g). From 1.08 g (1.97 mmol) of the compound from Example 22f), 915 mg of the title compound resulted as a solid, yellow foam.

$R_f$ (SiO$_2$, CH$_2$Cl$_2$/MeOH/NH$_4$OH 10:1:0.1)=0.31 MS (ESI): 424 (M+H)$^+$.

h) 8-[6-Methoxy-2-propyloxy-3-(trans-4-trifluoromethylcinnamoylglycyl-N-methyl) aminobenzyloxy]-2-methylquinoline The title compound was prepared by reaction of the compound from Example 22g) and the compound from Example 2a) by the process given in Example 2b). From 150 mg (0.36 mmol) of the compound from Example 22e), 109 mg of the title compound resulted as a pale yellow-colored solid.

$R_f$ (SiO$_2$, CH$_2$Cl$_2$/MeOH/NH$_4$OH 10:1:0.1)=0.69 MS (ESI): 622 (M+H)$^+$.

Example 23

8-[2,6-Dithiomethyl-3-(trans-4-methoxycinnamoylglycyl-N-methyl)amino-benzyloxy]-2-methylquinoline a) 8-(2,6-Dithiomethyl-3-nitrobenzyloxy)-2-methylquinoline A solution of 5.0 g (13.8 mmol) of 8-(2,6-dichloro-3-nitrobenzyloxy)-2-methylquinoline (disclosed in EP-A-622 361) and 1.93 g (27.6 mmol) of sodium thiomethylate in 50 ml of abs. DMF was stirred under an argon atmosphere at RT for 48 h. The reaction solution was poured onto water, and the crystals deposited were filtered off with suction, washed with H$_2$O, and dried. Purification by column chromatography on SiO$_2$ (CH$_2$Cl$_2$/EA/toluene 20:1:5) yielded 4.4 g of the title compound as yellow crystals.

$R_f$ (SiO$_2$, EA/n-heptane 1:1)=0.31 MS (ESI): 387 (M+H)$^+$.

b) 8-(2-2,6-Dithiomethyl-3-aminobenzyloxy)-2-methylquinoline

The title compound was prepared from the compound of Example 23a) by the process given in Example 1d). From 4.0 g (10.4 mmol) of the compound from Example 23a), 3.48 g of the title compound resulted as a yellow solid.

$R_f$ (SiO$^2$, EA/n-heptane 1:1)=0.25 MS (DCI): 357 (M+H)$^+$.

c) 8-[2,6-Dithiomethyl-3-(N-phthaloylglycyl) aminobenzyloxy]-2-methylquinoline

The title compound was prepared from the compound of Example 23b) by the process given in Example 1e). From 3.40 g (9.6 mmol) of the compound from Example 23b), 2.30 g of the title compound resulted in the form of a beige foam.

$R_f$ (SiO$_2$, EA/n-heptane 1:1)=0.28 MS (FAB): 544 (M+H)$^+$.

d) 8-[2,6-Dithiomethyl-3-(N-phthaloylglycyl-N-methyl) aminobenzyloxy]-2-methylquinoline The title compound was prepared from the compound of Example 23c) by the process given in Example 1f). From 2.20 g (4.10 mmol) of the compound from Example 23c), 1.70 g of the title compound resulted as a yellow solid.

$R_f$ (SiO$_2$, EA/heptane 1:1)=0.16 MS (FAB): 558 (M+H)$^+$.

e) 8-[2,6-Dithiomethyl-3-(N-glycyl-N-methyl) aminobenzyloxy]-2-methylquinoline

The title compound was prepared from the compound of Example 23d) by the process given in Example 1g). From 1.60 g (2.90 mmol) of the compound from Example 23d), 1.06 g of the title compound resulted as a beige, solid foam.

$R_f$ (SiO$_2$, EA/MeOH 1:1)=0.05 MS (FAB): 428 (M+H)$^+$.

e) 8-[2,6-Dithiomethyl-3-(trans-4-methoxycinnamoylglycyl-N-methyl)-aminobenzyloxy]-2-methylquinoline The title compound was prepared by reaction of the compound from Example 23e) and 4-methoxycinnamic acid by the process given in Example 10i). From 200 mg (0.47 mmol) of the compound from Example 23e), 72 mg of the title compound resulted as an amorphous solid.

$R_f$ (SiO$_2$, EA)=0.31 MS (FAB):588 (M+H)$^+$.

Example 24

8-[2,6-Dithiomethyl-3-(3-(6-acetylaminopyridin-3-yl)acryloylglycyl-N-methyl)aminobenzyloxy]-2-methylquinoline The title compound was prepared by reaction of the compound from Example 23e) with the acid chloride derivative of (E)-3-(6-acetylamino-3-pyridyl)acrylic acid by the process described in Example 2b). From 150 mg (0.35 mmol) of the compound from Example 23e), 68 mg of the title compound resulted.

$R_f$(SiO$_2$, EA(MeOH 10:1)=0.33 MS (ESI): 616 (M+H)$^+$.

Example 25

8-[2,6-Dichloro-3-[N-(4-aminobutylaminocarbonylglycyl-N-methyl)amino-benzyloxy]-1,2-dimethyl-1,2,3,4-tetrahydroquinoline bistrifluoroacetate a) 1,2-Dimethyl-8-hydroxy-1,2,3,4-tetrahydroquinoline 7.50 g (47.0 mmol) of 8-hydroxy-2-methylquinoline were hydrogenated in an autoclave in the presence of 0.75 g of PtO$_2$ in 60 ml of methanol at 4 bar of H$_2$ and a temperature of 50° C. for 24 h. The reaction solution was filtered, and the filtrate was concentrated to dryness. The residue of 2-methyl-8-hydroxy-1,2,3,4-tetrahydroquinoline obtained was dissolved in 60 ml of ethanol, 3.85 ml of 37% strength formaldehyde solution and 1.1 g of Pd/C (10% strength) were added, and the reaction mixture obtained was hydrogenated in an autoclave at 4 bar of H$_2$ and a temperature of 50° C. again for 24 h. It was filtered, the filtrate was concentrated, and the residue was purified by chromatography on SiO$_2$ (EA/n-heptane 1:4). 1.56 g of the title compound were obtained.

$R_f$(SiO$_2$, EA/n-heptane 1:4)=0.27 MS (DCI): 178 (M+H).

b) 8-(2,6-Dichloro-3-nitrobenzyloxy)-1,2-dimethyl-1,2,3, 4-tetrahydroquinoline

The title compound was prepared by reaction of the compound from Example 25a) and 2,6-dichloro-3-nitrobenzyl bromide (disclosed in EP-A-622 361) by the process given in Example 1c). From 1.4 g (7.90 mmol) of the compound from Example 25a), 1.20 g of the title compound resulted as an amorphous solid.

$R_f$ (SiO$_2$, EA/n-heptane 1:4)=0.31 MS (ESI): 381 (M+H)$^+$.

c) 8-(3-Amino-2,6-dichlorobenzyloxy)-1,2-dimethyl-1,2, 3,4-tetrahydro-quinoline

The title compound was prepared from the compound of Example 25b) by the process given in Example 1d). From 1.15 g (3.03 mmol) of the compound of Example 25b), 0.87 g of the title compound was obtained.

$R_f$ (SiO$_2$, EA/n-heptane 1:1)=0.17 MS (ESI): 351 (M+H)$^+$.

d) 8-[2,6-Dichloro-3-(N-phthaloylglycyl) aminobenzyloxy]-1,2-dimethyl-1,2,3,4-tetrahydroquinoline The title compound was prepared from the compound of Example 25c) by the process given in Example 1e). From 1.10 g (3.14 mmol) of the compound from Example 25c), 1.27 g of the title compound resulted.

$R_f$ (SiO$_2$, EA/n-heptane 1:2)=0.21 MS (ESI): 538 (M+H)$^+$.

e) 8-[2,6-Dichloro-3-(N-phthaloylglycyl-N-methyl) aminobenzyloxy]-1,2-dimethyl-1,2,3,4-tetrahydroquinoline The title compound was prepared from the compound of Example 25d) by the process given in Example 1f). From 1.25 g (2.32 mmol) of the compound from Example 25d), 1.21 g of the title compound resulted.

$R_f$ (SiO$_2$, EA/n-heptane 2:1)=0.16 MS (ESI): 552 (M+H)$^+$.

f) 8-[2,6-Dichloro-3-(N-glycyl-N-methyl) aminobenzyloxy]-1,2-dimethyl-1,2,3,4-tetrahydroquinoline The title compound was prepared from the compound of Example 25e) by the process given in Example 1g). From 1.20 g (2.17 mmol) of the compound from Example 25e), 0.67 g of the title compound resulted as an amorphous solid.

$R_f$ (SiO$_2$, EA/MeOH 10:1)=0.10 MS (ESI): 422 (M+H)$^+$.

g) 8-[2,6-Dichloro-3-(N-(4-aminobutylaminocarbonyl) glycyl-N-methyl)aminobenzyloxy]-1,2-dimethyl-1,2, 3,4-tetrahydroquinoline bistrifluoroacetate The title compound was prepared from the compound of Example 25f) by the processes given in Examples 6a and 6b). From 0.35 g (0.83 mmol) of the compound from Example 25f), 122 mg of the title compound resulted.

$R_f$ (SiO$_2$, CH$_2$Cl$_2$/MeOH/NH$_4$OH 10:1:0.1)=0.04 MS (FAB): 536 (M+H)$^+$.

Example 26

4-Chloro-2-thiomethyl-N-(2-phenylethyl)-N-methyl-3-[(2-methylquinolin-8-yl)oxymethyl] benzenesulfonamide a) 4-Chloro-2-thiomethyl-N-(l1,1-dimethylethyl)-N-methyl-3-[(2-methyl-quinolin-8-yl)oxymethyl] benzenesulfonamide The title compound was prepared from 2,4-dichloro-N-(1,1-dimethylethyl)-N-methyl-3-[(2-methylquinolin-8-yl) oxymethyl]benzenesulfonamide (disclosed in WO 96-40639) by the process given in Example 16a).

MS (FAB): 429 (M+H)$^+$.

b) 4-Chloro-2-thiomethyl-N-methyl-3-[(2-methylquinolin-8-yl)-oxymethyl]-benzenesulfonamide 3.0 g (7.0 mmol) of the compound from Example 26a) were stirred at RT for 1 h in 70 ml of 5N HCl solution. The reaction mixture was poured onto ice, and the precipitate deposited was filtered off with suction. After dissolving in 2N HaOH solution, it was extracted with CH$_2$Cl$_2$. The organic phase was washed with H$_2$O, dried over MgSO$_4$, and concentrated to dryness. 1.9 g of the title compound resulted.

MS (FAB): 373 (M+H)$^+$.

c) 4-Chloro-2-thiomethyl-N-(2-phenylethyl)-N-methyl-3-[(2-methylquinolin-8-yl)oxymethyl] benzenesulfonamide 500.0 mg (1.34 mmol) of the compound from Example 26b) were dissolved in 5 ml of abs. DMF and treated with 64 mg (1.34 mmol) of NaH (50% strength). After stirring at RT for 10 min, 0.31 g (1.34 mmol) of 2-iodoethylbenzene was added, and the mixture was stirred at RT for 8 h. Water was added, and the mixture was extracted several times with EA. The EA extracts were washed with H$_2$O, dried over MgSO$_4$, and concentrated. Purification of the residue by column chromatography on SiO$_2$ (EA/heptane 1:5) yielded 72 mg of the title compound.

MS (FAB): 477 (M+H)$^+$.

While the invention has been described in terms of various preferred embodiments and specific examples, those skilled in the art will recognize that various changes and modifications can be made without departing from the spirit and scope of the invention, as defined in the appended claims.

We claim:

1. A compound of formula (I):

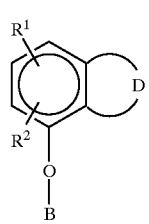

(I)

wherein:

D is a radical of formula (II) or (III):

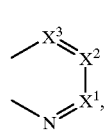

(II)

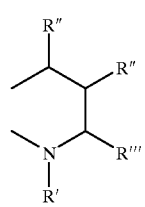

(III)

wherein:

$X^1$ is —C—R$^6$;

$X^2$ is —C—R$^7$;

$X^3$ is —C—R$^8$;

B is a radical of formula (VIII)

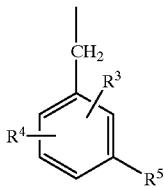

(VIII)

$R^1$ and $R^2$, which may be identical or different, are
(a) hydrogen,
(b) halogen, or
(c) $(C_1-C_3)$-alkyl;

$R^3$ and $R^4$, which may be identical or different, are
(a) hydrogen,
(b) halogen,
(c) cyano,
(d) $(C_1-C_3)$-alkyl,
(e) —O—$(C_1-C_3)$-alkyl,
(f) —S—$(C_1-C_3)$-alkyl,
 wherein, in the radicals mentioned under (d), (e), or (f), 1 to 5 of the hydrogen atoms present in the alkyl groups can be replaced by halogen atoms,
(g) —OH,
(h) tetrazolyl,
(i) —CONHR$^9$, or
(j) —COOR$^9$;

$R^5$ is
(a) nitro,
(b) amino,
(c) a radical of formula (IV)

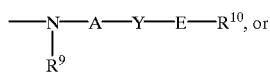

(IV)

(d) a radical of formula (V)

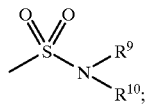

(V)

$R^6$, $R^8$, and R''', which may be identical or different, are
(a) hydrogen,
(b) halogen,
(c) $(C_1-C_4)$-alkyl,
(d) $(C_1-C_4)$-alkoxy,
(e) amino,
(f) $(C_1-C_4)$-alkylamino,
(g) hydroxyl,
(h) $(C_6-C_{12})$-aryl,
(i) $(C_6-C_{12})$-aryl-$(C_1-C_4)$-alkandiyl, or
(j) —COOR$^9$;

$R^7$, R', and R'', which may be identical or different, are
(a) hydrogen, or
(b) $(C_1-C_4)$-alkyl,
 wherein each R'' in formula (III) may be identical or different;

$R^9$ is
(a) hydrogen,
(b) $(C_1-C_4)$-alkyl,
(c) $(C_2-C_5)$-alkenyl, or
(d) $(C_6-C_{12})$-aryl-$(C_1-C_3)$-alkandiyl;

A is a bivalent radical of an aminocarboxylic acid;

Y is

1.
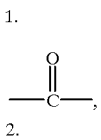

2.
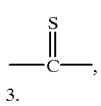

3.

E is
(a) $(C_2-C_5)$-alkenediyl,
(b) $(C_1-C_7)$-alkanediyl,
(c) $(C_3-C_{10})$-cycloalkanediyl, or
(d) —$(CH_2)_m$—$T_o$—$(CH_2)_n$—, wherein m, n, and o are defined such that —$(CH_2)_m$—$T_o$—$(CH_2)_n$— is not a $(C_1-C_7)$-alkanediyl or a single bond,
wherein the radicals mentioned under (a) through (d) optionally can be substituted;

T is
(a) O,
(b) S, or
(c) —NR$^{15}$;

m and n, which may be identical or different, are each an integer from 0–6;

o is 0 or 1;

$R^{10}$ is
(a) hydrogen,
(b) $(C_1-C_5)$-alkyl,
(c) $(C_6-C_{10})$-aryl,
(d) $(C_1-C_3)$-alkandiyl-$(C_6-C_{10})$-aryl, or
(e) a heteroaryl group,
 wherein (c), (d), and (e) can optionally be substituted by one or more groups;

$R^{15}$ is
(a) hydrogen,
(b) —C(O)—$(C_1-C_3)$-alkyl, or
(c) $(C_1-C_3)$-alkyl;

or a physiologically tolerable salt thereof;

with a first proviso that formula (I) does not include a compound wherein D is a radical of formula (II), $R^3$ and $R^4$ are simultaneously halogen, $(C_1-C_3)$-alkyl, —O—$(C_1-C_3)$-alkyl, or a combination thereof, and $R^3$ and $R^4$ are hydrogen in combination with halogen, $(C_1-C_3)$-alkyl, —O—$(C_1-C_3)$-alkyl, or a combination thereof, (α) with a first exception to the first proviso being that formula (I) does include a compound
 wherein D is a radical of formula (II) and $R^5$ is a radical of formula (IV),
 wherein $R^{10}$ is a heteroaryl group or a radical of formula (VI)

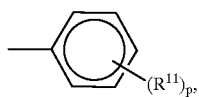

(VI)

wherein p is an integer from 1 to 3, and
R$^{11}$ is (a) (C$_1$–C$_5$)-alkyl, wherein the hydrogen atoms are partially or completely replaced by fluorine or chlorine, or (b) (C$_1$–C$_5$)-alkoxy, wherein the hydrogen atoms are partially or completely replaced by fluorine or chlorine, and (β) with a second exception to the first proviso being that formula (I) does include a compound wherein D is a radical of formula (II) and R$^5$ is a radical of formula (V);

said first and second exceptions to the first proviso do not include a compound of formula (I) wherein R$^{10}$ has the formula (VI), R$^3$ and R$^4$ are identically or differently hydrogen and halogen, and wherein D is a radical of formula (II) and R$^5$ is a radical of formula (V), R$^3$ and R$^4$ are halogen;

said first and second exceptions to the first proviso do not include a compound of formula (I) wherein D is a radical of formula (II), R$^5$ is a radical of formula (IV), R$^9$ is hydrogen or (C$_1$–C$_4$)-alkyl, Y is —CO—, E is (C$_2$–C$_5$)-alkenediyl, (C$_1$–C$_6$)-alkanediyl, (CH$_2$)$_m$—NH— where m is 0 or 1, or —CH$_2$—S—, and R$^{10}$ is a heteroaryl group;

said first and second exceptions to the first proviso do not include a compound of formula (I) wherein D is a radical of formula (II), R$^5$ is a radical of formula (IV), R$^9$ is hydrogen or (C$_1$–C$_4$)-alkyl, Y is —CO—, E is (C$_2$–C$_5$)-alkenediyl or —NH—, and R$^{10}$ is pyridyl monosubstituted with —COOH or —CONR$^{13}$R$^{14}$ wherein R$^{13}$ is hydrogen, (C$_1$–C$_5$)-alkyl, (C$_2$–C$_5$)-alkenyl, or (C$_6$–C$_{12}$)-aryl, and R$^{14}$ is hydrogen;

said first and second exceptions to the first proviso do not include a compound of formula (I) wherein D is a radical of formula (II), R$^5$ is a radical of formula (IV), R$^9$ is methyl, Y is —CO—, E is —NH—CH$_2$—, and R$^{10}$ is unsubstituted pyridyl; and with a second proviso that when D is a radical of formula (II) and R$^5$ is nitro or amino, R$^3$ and R$^4$ cannot simultaneously be hydrogen.

2. A compound of formula (I) as claimed in claim 1, wherein:

X$^1$ is —C—R$^6$;
X$^2$ is —C—R$^7$;
X$^3$ is —C—R$^8$;
R$^1$ and R$^2$, which may be identical or different, are hydrogen, a methyl group, or an ethyl group;
R', R''', R$^6$, R$^7$, and R$^8$, which may be identical or different, are hydrogen or a (C$_1$–C$_4$)-alkyl group;
R'' is hydrogen;
A is the bivalent radical of the amino acid glycine or alanine;

Y is

E is
(a) (C$_2$–C$_5$)-alkenediyl,
(b) (C$_1$–C$_7$)-alkanediyl, or
(c) —(CH$_2$)$_m$—T$_o$—(CH$_2$)$_n$—, wherein m, n, and o are defined such that —(CH$_2$)$_m$—T$_o$—(CH$_2$)$_n$— is not a (C$_1$–C$_7$)-alkanediyl, wherein the radicals mentioned under (a), (b), and (c) are optionally substituted by a group selected from —OR$^{12}$, —NO$_2$, —CN, —CO$_2$R$^9$, —NR$^{13}$R$^{14}$, —SO$_3$R$^{12}$, —SO$_2$NR$^{13}$R$^{14}$, and —CONR$^{13}$R$^{14}$, wherein R$^{12}$ and R$^{13}$, which may be identical or different, are
(a) hydrogen,
(b) (C$_1$–C$_5$)-alkyl,
(c) (C$_2$–C$_5$)-alkenyl,
(d) (C$_6$–C$_{12}$)-aryl,
(e) (C$_6$–C$_{12}$)-aryl-(C$_1$–C$_5$)-alkandiyl,
(f) (C$_3$–C$_{10}$)-cycloalkyl,
(g) (C$_3$–C$_{10}$)-cycloalkyl-(C$_1$–C$_2$)-alkandiyl,
(h) —C(O)—O—(C$_1$–C$_5$)-alkyl, or
(i) —C(O)NH—(C$_1$–C$_5$)-alkyl; and
R$^{14}$ is
(a) hydrogen,
(b) —C(O)—O—(C$_1$–C$_4$)-alkyl, or
(c) —C(O)—O—(C$_1$–C$_3$)-alkyl-(C$_6$–C$_{10}$)-aryl;

T is O or NH;
m and n, which may be identical or different, are each an integer from 0–3;
p is an integer 1 or 2;
R$^{11}$ is —CF$_3$ or —OCF$_3$; and
R$^{15}$ is hydrogen, a methyl group, or an ethyl group;
or a physiologically tolerable salt thereof.

3. A compound of formula (I) as claimed in claim 2, wherein R$^{12}$ and R$^{13}$, which may be identical or different, are (a) hydrogen, (b) (C$_1$–C$_5$)-alkyl, (c) (C$_6$–C$_{12}$)-aryl, or (d) (C$_6$–C$_{12}$)-aryl-(C$_1$–C$_3$)-alkandiyl-; or a physiologically tolerable salt thereof.

4. A compound of formula (I) as claimed in claim 2, wherein D is formula (II); or a physiologically tolerable salt thereof.

5. A compound of formula (I) as claimed in claim 1, wherein:

D is a radical of formula (II) or (III);
B is a radical of formula (IX):

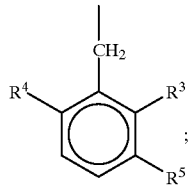

(IX)

X$^1$ is —C—CH$_3$;
X$^2$ is —C—H;
X$^3$ is —C—H;
R' is methyl;
R'' is hydrogen;

R''' is methyl;
R$^1$ and R$^2$ are each hydrogen;
R$^3$ and R$^4$, which may be identical or different, are chlorine, cyano, methyl, —O—methyl, —S—methyl, —OH, tetrazolyl, or —CONH$_2$;
R$^5$ is
  (a) nitro,
  (b) amino,
  (c) a radical of formula (X)

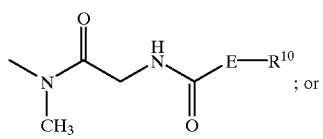
(X)

(d) a radical of formula (V)

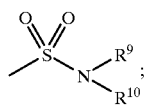
(V)

R$^9$ is hydrogen, methyl, ethyl, n-propyl, i-propyl, n-butyl, i-butyl, or benzyl;
E is
  (a) (C$_2$–C$_5$)-alkenediyl,
  (b) (C$_1$–C$_7$)-alkanediyl, or
  (c) —(CH$_2$)$_m$—T$_o$—(CH$_2$)$_n$—, wherein m, n, and o are defined such that —(CH$_2$)$_m$—T$_o$—(CH$_2$)$_n$— is not a (C$_1$–C$_7$)-alkanediyl, wherein these radicals are optionally substituted by a group selected from —OR$^{12}$, —CO$_2$R$^9$, —NR$^{13}$R$^{14}$, and —CONR$^{13}$R$^{14}$;
T is O or NH;
m and n, which may be identical or different, are each a number from 0 to 3;
o is 0 or 1;
R$^{10}$ is
  (a) hydrogen,
  (b) (C$_1$–C$_5$)-alkyl,
  (c) phenyl,
  (d) benzyl, or
  (e) a heteroaryl group containing 4 to 7 carbon atoms, wherein (c), (d), and (e) can optionally be substituted by one or two groups selected from (C$_1$–C$_5$)-alkyl, (C$_1$–C$_5$)-alkoxy, —CF$_3$, —OCF$_3$, —NR$^{13}$R$^{14}$, —NR$^{13}$CO—R$^{16}$, and —CO$_2$R$^9$;
R$^{11}$ is —CF$_3$ or —OCF$_3$;
R$^{12}$ and R$^{13}$, which may be identical or different, are
  (a) hydrogen,
  (b) (C$_1$–C$_5$)-alkyl,
  (c) (C$_2$–C$_5$)-alkenyl,
  (d) (C$_6$–C$_{12}$)-aryl,
  (e) (C$_6$–C$_{12}$)-aryl-(C$_1$–C$_5$)-alkandiyl,
  (f) (C$_3$–C$_{10}$)-cycloalkyl,
  (g) (C$_3$–C$_{10}$)-cycloalkyl-(C$_1$–C$_2$)-alkandiyl,
  (h) —C(O)—O—(C$_1$–C$_5$)-alkyl, or
  (i) —C(O)NH—(C$_1$–C$_5$)-alkyl;
R$^{14}$ is
  (a) hydrogen,
  (b) —C(O)—O—(C$_1$–C$_4$)-alkyl, or
  (c) —C(O)—O—(C$_1$–C$_3$)-alkyl-(C$_6$–C$_{10}$)-aryl; and R$^{16}$ is
  (a) (C$_1$–C$_3$)-alkyl,
  (b) (C$_6$–C$_{12}$)-aryl, or
  (c) a heteroaryl group,
    wherein these radicals can optionally be substituted by one or more groups;
or a physiologically tolerable salt thereof.

6. A compound of formula (I) as claimed in claim 5, wherein D is formula (II); or a physiologically tolerable salt thereof.

7. A compound of formula (I) as claimed in claim 5, wherein R$^{10}$ is a furyl group or a pyridyl group; or a physiologically tolerable salt thereof.

8. A compound of formula (I) as claimed in claim 5, wherein
R$^{12}$ and R$^{13}$, which may be identical or different, are hydrogen, methyl, ethyl, phenyl, or benzyl;
R$^{14}$ is hydrogen, —C(O)—O—C—(CH$_3$)$_3$, or —C(O)—O—CH$_2$-phenyl; and
R$^{16}$ is methyl, ethyl, phenyl, or a heteroaryl group containing 4 to 7 carbon atoms in the ring structure, wherein these radicals can optionally be substituted by one or two groups selected from —NR$^{13}$R$^{14}$ or —CO$_2$R$^9$;
or a physiologically tolerable salt thereof.

9. A compound of formula (I) as claimed in claim 5, wherein the R$^{16}$ group is substituted by one or more groups selected from halogen, —CN, —NO$_2$, —NR$^{13}$R$^{14}$, and —CO$_2$R$^9$;
or a physiologically tolerable salt thereof.

10. A compound of formula (I) as claimed in claim 1, wherein D is formula (II); or a physiologically tolerable salt thereof.

11. A compound of formula (I) as claimed in claim 1, wherein A is a member selected from methionine, alanine, phenylalanine, tyrosine, o-methylthyrosine, β-(2-thienyl) alanine, glycine, cyclohexylalanine, leucine, isoleucine, valine, norleucine, phenylglycine, serine, cysteine, aminopropionic acid, and aminobutyric acid; or a physiologically tolerable salt thereof.

12. A compound of formula (I) as claimed in claim 1, wherein the E substituent is substituted by one or more groups selected from —O—R$^{12}$, —NO$_2$, —CN, —CO$_2$R$^9$, —NR$^{13}$R$^{14}$, —SO$_3$R$^{12}$, —SO$_2$NR$^{13}$R$^{14}$, and —CONR$^{13}$R$^{14}$, wherein
R$^{12}$ and R$^{13}$, which may be identical or different, are
  (a) hydrogen,
  (b) (C$_1$–C$_5$)-alkyl,
  (c) (C$_2$–C$_5$)-alkenyl,
  (d) (C$_6$–C$_{12}$)-aryl,
  (e) (C$_6$–C$_{12}$)-aryl-(C$_1$–C$_5$)-alkandiyl,
  (f) (C$_3$–C$_{10}$)-cycloalkyl,
  (g) (C$_3$–C$_{10}$)-cycloalkyl-(C$_1$–C$_2$)-alkandiyl,
  (h) —C(O)—O—(C$_1$–C$_5$)-alkyl, or
  (i) —C(O)NH—(C$_1$–C$_5$)-alkyl; and
R$^{14}$ is
  (a) hydrogen,
  (b) —C(O)—O—(C$_1$–C$_4$)-alkyl, or
  (c) —C(O)—O—(C$_1$–C$_3$)-alkyl-(C$_6$–C$_{10}$)-aryl;
or a physiologically tolerable salt thereof.

13. A compound of formula (I) as claimed in claim 1, wherein the R$^{10}$ substituent is selected from a (C$_6$–C$_{10}$)-aryl group, a (C$_1$–C$_3$)-alkandiyl-(C$_6$–C$_{10}$)-aryl group, or a heteroaryl group; or a physiologically tolerable salt thereof.

14. A compound of formula (I) as claimed in claim 13, wherein the R$^{10}$ group is substituted by one or more groups selected from halogen, —CN, —NO$_2$, (C$_1$–C$_5$)-alkylthio, —NR$^{13}$R$^{14}$, —NR$^{13}$CO—R$^{16}$, —CO$_2$R$^9$, —SO$_3$R$^{12}$, —SO$_2$NR$^{13}$R$^{14}$, —OR$^{12}$, (C$_1$–C$_6$)-alkyl, (C$_6$–C$_{10}$)-aryl, (C$_2$–C$_5$)-alkenyl, and (C$_1$–C$_5$)-alkoxy, wherein the alkyl, aryl, alkenyl, and alkoxy radicals are optionally partially or completely substituted by halogen, wherein R$^{12}$ and R$^{13}$, which may be identical or different, are
(a) hydrogen,
(b) (C$_1$–C$_5$)-alkyl,
(c) (C$_2$–C$_5$)-alkenyl,
(d) (C$_6$–C$_{12}$)-aryl,
(e) (C$_6$–C$_{12}$)-aryl-(C$_1$–C$_5$)-alkandiyl,
(f) (C$_3$–C$_{10}$)-cycloalkyl,
(g) (C$_3$–C$_{10}$)-cycloalkyl- (C$_1$–C$_2$)-alkandiyl,
(h) —C(O)—O—(C$_1$–C$_5$)-alkyl, or
(i) —C(O)NH—(C$_1$–C$_5$)-alkyl;

R$^{14}$ is
(a) hydrogen,
(b) —C(O)—O—(C$_1$–C$_4$)-alkyl, or
(c) —C(O)—O—(C$_1$–C$_3$)-alkyl-(C$_6$–C$_{10}$)-aryl; and R$^{16}$ is
(a) (C$_1$–C$_3$)-alkyl,
(b) (C$_6$–C$_{12}$)-aryl, or
(c) a heteroaryl group,
wherein these radicals can optionally be substituted by one or more groups;

or a physiologically tolerable salt thereof.

15. A process for preparing a compound of formula (I) as claimed in claim 1, or a physiologically tolerable salt thereof, comprising:

a) reacting a compound of formula (XI)

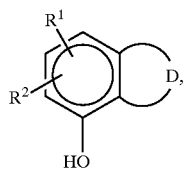

(XI)

in the presence of at least one metal hydride or at least one alkali metal carbonate, in an inert solvent, at a temperature from 0° C. to 60° C., with a compound of formula (XII)

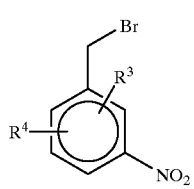

(XII)

to produce a compound of formula (XIII)

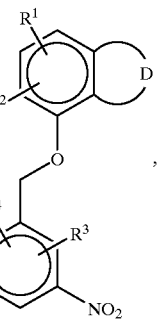

(XIII)

b) reducing the compound of formula (XIII) with the aid of a transition metal halide to a compound of formula (XIV)

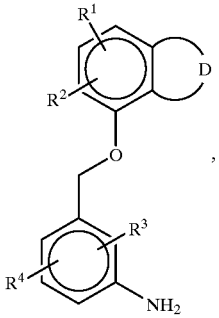

(XIV)

c) reacting the compound of formula (XIV) with an activated, protected aminocarboxylic acid derivative of A, in an inert solvent in the presence of a base, to obtain a compound of formula (XV)

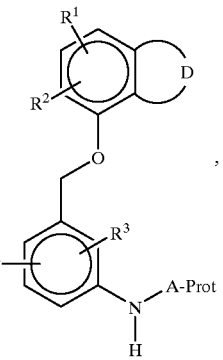

(XV)

in which Prot is an amino-protective group;

d) reacting the compound of formula (XV), after action of an alkali metal hydride, an alkali metal carbonate or an alcoholate in an inert solvent, with R$^9$X, wherein X is a leaving group, to obtain a compound of formula (XVI)

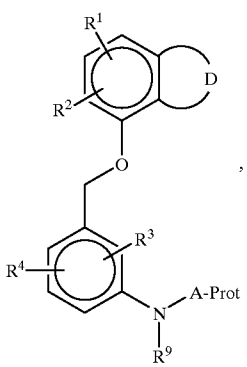

(XVI)

e) converting the compound of formula (XVI), under sufficient conditions, into a compound of formula (XVII)

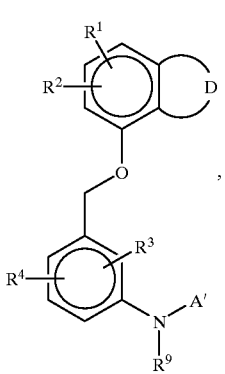

(XVII)

wherein A' is a radical of an aminocarboxylic acid;

f) reacting the compound of formula (XVII) under sufficient conditions to produce the compound of formula (I); and g) optionally, converting the compound of formula (I) into a physiologically tolerable salt thereof.

16. A process according to claim 15, wherein Prot represents a phthaloyl protecting group, and the conversion of the compound of formula (XVI) into the compound of formula (XVII) includes hydrazinolysis of compound (XVI) in ethanol, at a temperature from 20° C. up to the boiling point.

17. A process according to claim 15, wherein the compound of formula (XVII) is converted into the compound of formula (I) by reacting the compound of formula (XVII) with an activated carboxylic acid derivative and a sulfonic acid derivative $R^{10}$—E—Y—OH, in an organic solvent, in the presence of an inorganic or organic base, at a temperature from 0° C. to reflux, to produce the compound of formula (I).

18. A process according to claim 15, wherein the compound of formula (XVII) is converted into the compound of formula (I) by reacting the compound of formula (XVII) with an amine $R^{10}$—E—$NH_2$ or an alcohol $R^{10}$—E—OH, in an inert solvent to produce the compound of formula (I), wherein prior to this reacting procedure between the compound of formula (XVII) and the amine or the alcohol, the compound of formula (XVII) or the amine or the alcohol is reacted with a doubly activated carbonyl compound.

19. A process according to claim 15, wherein the compound of formula (XVII) is converted into the compound of formula (I) by reacting the compound of formula (XVII) with an isocyanate or an isothiocyanate in an inert solvent, to produce the compound of formula (I).

20. A pharmaceutical composition, comprising a compound according to formula I as claimed in claim 1 or a physiologically tolerable salt thereof; and a pharmaceutically utilizable carrier or excipient.

21. A method for treating liver cirrhosis, comprising administering to a subject an effective amount of the pharmaceutical composition according to claim 20.

22. A method for treating liver cirrhosis, comprising administering to a subject an effective amount of the compound according to claim 1 or a physiologically tolerable salt thereof.

* * * * *